United States Patent
Li et al.

(10) Patent No.: US 11,371,074 B2
(45) Date of Patent: Jun. 28, 2022

(54) METHOD AND SYSTEM FOR DETERMINING COPY NUMBER VARIATION

(71) Applicant: BGI GENOMICS CO., LTD., Shenzhen (CN)

(72) Inventors: Xuchao Li, Shenzhen (CN); Shengpei Chen, Shenzhen (CN); Fang Chen, Shenzhen (CN); Weiwei Xie, Shenzhen (CN); Jian Wang, Shenzhen (CN); Jun Wang, Shenzhen (CN); Huanming Yang, Shenzhen (CN); Xiuqing Zhang, Shenzhen (CN)

(73) Assignee: BGI Genomics Co., Ltd., Shenzhen (CN)

( * ) Notice: Subject to any disclaimer, the term of this patent is extended or adjusted under 35 U.S.C. 154(b) by 1014 days.

(21) Appl. No.: 15/881,902

(22) Filed: Jan. 29, 2018

(65) Prior Publication Data
US 2018/0148765 A1    May 31, 2018

Related U.S. Application Data

(63) Continuation of application No. 14/389,898, filed as application No. PCT/CN2012/073545 on Apr. 5, 2012, now abandoned.

(51) Int. Cl.
| C12Q 1/68 | (2018.01) |
| G16B 30/00 | (2019.01) |
| G16C 99/00 | (2019.01) |
| C12Q 1/6869 | (2018.01) |
| G16B 30/10 | (2019.01) |
| G16B 15/00 | (2019.01) |

(52) U.S. Cl.
CPC ............ *C12Q 1/68* (2013.01); *C12Q 1/6869* (2013.01); *G16B 30/00* (2019.02); *G16B 30/10* (2019.02); *G16C 99/00* (2019.02); *C12Q 2535/122* (2013.01); *C12Q 2537/165* (2013.01); *G16B 15/00* (2019.02)

(58) Field of Classification Search
None
See application file for complete search history.

(56) References Cited

FOREIGN PATENT DOCUMENTS

| CN | 101449161 A | 6/2009 |
| WO | 2004044225 A2 | 5/2004 |

OTHER PUBLICATIONS

Wald et al., "On a Test Whether Two Samples are from the Same Population", Annals of Math Stats., vol. 11, No. 2, pp. 147-162 (Jun. 1940).
Illumina/Solexa, Innovative Technollogies, downloaded from web page: http://www.illumina.com, Download date: May 2017, original posting date 2017, 2 pages.
Metzker, "Sequencing Technologies—The Next Generation", Nature Review Gen., vol. 11, pp. 31-46 (Jan. 2010).
Rusk, "Cheap Third-Generation Sequencing", Nature America., vol. 6, No. 4, pp. 244-245 (Apr. 2009).
Hamady et al., Error-Correcting Barcoded Primers Allow Hundreds of Samples to be Pyrosequenced in Multiplex, vol. 5, No. 3, pp. 235-237 (Mar. 2008).
Nord et al., "Accurate and Exact CNV Identification from Targeted High-Throughput Sequence Data", BMC Genomics, vol. 12, No. 184, pp. 1-10 (2011).
Yoon, et al., "Sensitive and Accurate Detection of Copy Number Variants Using Read Depth of Coverage", Genome Res., vol. 19, pp. 1586-1592 (2009).
Klambauer et al., "cn.MOPS:Mixture of Poissons for Discoveoring Copy Number Variations in Next-Generation Sequencing Data with a Low False Discovery Rate", Nucleic Acids Res, vol. 40, No. 9, pp. 1-14 (Feb. 2012).
Xi et al., "Detecting Structural Variations in the HumanGenome usingNext Generationsequencing", Brief Funct. Genomics, vol. 9, No. 5, pp. 405-415 (2011).
Chiang et al., "High-Resolution Mapping of Copy-Number Alterations with Massively Parallel Sequencing", Nat. Methods, vol. 6, No. 3, 7 pages (Jan. 2009).

*Primary Examiner* — Joseph Woitach
(74) *Attorney, Agent, or Firm* — Ice Miller LLP

(57) ABSTRACT

Disclosed are a method and a system for determining genome copy number variation, which relates to the technical field of bioinformatics. The method and the system have clinical feasibility, and can precisely detect a micro-deletion/micro-duplication area of 0.5 M under the situation of using data of about 50 M.

10 Claims, 12 Drawing Sheets

METHOD AND SYSTEM FOR DETERMINING COPY NUMBER VARIATION

CROSS-REFERENCE TO RELATED APPLICATION

This application is a continuation of U.S. patent application Ser. No. 14/389,898, filed on Oct. 1, 2014 as a Section 371 of International Application No. PCT/CN2012/073545, filed on Apr. 5, 2012, which was published in the Chinese language on Oct. 10, 2013 under International Publication No. WO 2013/149385, the entire contents of the aforementioned applications are incorporated herein by reference.

TECHNICAL FIELD

Embodiments of the present invention generally relate to the field of bioinformatics, more particularly to a method of detecting a copy number variation (CNV) and a system thereof.

BACKGROUND

CNV is one form of genomic structural variation. A narrow definition of CNV often refers to a copy number change of a DNA fragment in a chromosome. Types and reasons for this form of genomic structural variation may include: 1. deletion (terminal deletion, interstitial deletion); 2. translocation (reciprocal translocation, Robertsonian translocation); 3. Inversion; 4. ring chromosome; 5. dicentric chromosome; 6. insert, etc. A broader definition of CNV also includes, for example, structural variations such as chromosome aneuploidy and partial aneuploidy.

Presently available methods for detecting the copy number variation mainly include high resolution chromosome karyotype analysis, FISH (fluorescence in situ hybridization), Array CGH (array comparative genomic hybridization), MLPA (Multiplex Ligation-Dependent Probe Amplification), PCR (Polymerase Chain Reaction), etc, among which FISH detection is regarded as a gold standard for genetic diagnosis, which may effectively be used to detect most of known chromosomal deletions or repeats. However, these methods generally suffer from low efficiencies, particularly when used for whole-genome scans, which can consume large amounts of resources or may not be able to detect unknown CNV.

Therefore, there is an urgent need for a new method of detecting a copy number variation in order to characterize a known site and explore an unknown site in the genome.

SUMMARY

One technical problem to be solved by the present invention is to provide a method of detecting a copy number variation and a system thereof, which can accurately detect a copy number variation even including micro-deletion and micro-duplication.

Embodiments of a first general aspect of the present invention relate to a method of detecting a copy number variation. According to embodiments of the present invention, the method comprises the following steps:

obtaining reads from at least one part of a nucleic acid molecule of a sample, determining uniquely-mapped reads aligned to a (genomic) reference sequence based on the obtained reads, dividing the genomic reference sequence into a plurality of windows, and calculating the number of uniquely-mapped reads falling into each of the plurality of windows, subjecting the number of uniquely-mapped reads falling into each of the plurality of windows to a GC correction, and to a correction based on an expected number of uniquely-mapped reads adjusted by a control set to obtain a corrected number of uniquely-mapped reads, calculating a significance value of the difference between two numerical populations each consisting of the corrected numbers of uniquely-mapped reads falling into windows on each of the two sides of a demarcation point, the demarcation point being a starting point or an ending point of each of the plurality of windows, to thereby select the demarcation point having a smaller significance value as a candidate CNV breakpoint;

calculating a significance value of the difference between two numerical populations each consisting of the corrected number of uniquely-mapped reads falling into windows contained within each of two sequences, with one sequence ranging from a given CNV breakpoint to an adjacent upstream CNV breakpoint, and the other sequence ranging from the given CNV breakpoint to an adjacent downstream CNV breakpoint, and removing the candidate CNV breakpoint having the least significance at every turn and recalculating the significance value for the two candidate CNV breakpoints adjacent to the removed candidate CNV breakpoint, performing cyclic iteration until the significance values of all candidate CNV breakpoints are less than a termination threshold value, to thereby determine the CNV breakpoint.

Optionally, the method can further comprise a step of: subjecting the at least one part of the nucleic acid molecule of the sample to sequencing to obtain the reads.

Optionally, each of the plurality of windows can contain the same number of reference unique reads, or each of the plurality of windows can have the same length.

Optionally, the termination threshold value can be obtained based on the control set consisting of normal samples.

Optionally, the step of subjecting the number of uniquely-mapped reads falling into each of the plurality of windows to the GC correction and to a correction based on the expected number of uniquely-mapped reads adjusted by a control set to obtain the corrected number of uniquely-mapped reads can further comprise: grouping the plurality of windows based on a GC content, and obtaining a correction coefficient based on a mean value of the number of uniquely-mapped reads within one group and a mean value of the number of uniquely-mapped reads for all of the plurality of windows, and then subjecting the number of uniquely-mapped reads falling into each of the plurality of windows to the correction, to obtain the GC-corrected number of uniquely-mapped reads.

Optionally, the expected number of uniquely-mapped reads adjusted by the control set can be obtained by following steps:

calculating a ratio of the GC-corrected number of uniquely-mapped reads falling into each of the plurality of windows in the control set to the total number of uniquely-mapped reads;

obtaining a mean value of the ratios for all windows corresponding to the control set; and calculating the expect number of uniquely-mapped reads for each of the plurality of windows in the sample based on the obtained mean value of the ratios and the total number of uniquely-mapped reads in the sample.

Optionally, after the CNV breakpoint is determined, the method can further comprise:

subjecting a sequence between two CNV breakpoints to a confidence selection, wherein the confidence selection comprises steps of:

determining a confidence interval of the normal corrected number of uniquely-mapped reads using the control set, based on a distribution of the corrected number of uniquely-mapped reads; and determining an abnormality presenting in the sequence between the two CNV breakpoints, if the mean value of the corrected number of uniquely-mapped reads within the sequence is outside the confidence interval.

Optionally, the corrected number of uniquely-mapped reads can fit a normal distribution, and the confidence interval can be 95%.

Optionally, a cyclization with a single chromosome or a whole genome can be performed when selecting the candidate CNV breakpoint.

Optionally, the method can further comprise:

obtaining the sample from a human, the sample comprising amniotic fluid obtained by amniocentesis, villus obtained by chorionic villi sampling, umbilical cord blood obtained by percutaneous umbilical blood sampling, spontaneous miscarrying fetus tissue or human peripheral blood; and/or obtaining a genomic DNA of the sample by a DNA extraction method such as a salting-out method, a column chromatography method, a beads method, or a SDS method; and/or subjecting the genome DNA of the sample to random fragmenting by enzyme digestion, pulverization, ultrasound, or HydroShear method, to obtain DNA fragments; and/or subjecting the DNA fragments to single-end sequencing or pair-end sequencing, to obtain the reads of the DNA fragments.

Optionally, the method can further comprise adding different indexes to each of the DNA fragments of the samples, to distinguish different samples.

Embodiments of a second general aspect of the present invention provide a system for determining a copy number variation. According to embodiments of the present invention, the system can comprise:

a reads obtaining unit, for obtaining reads from at least one part of a nucleic acid molecule of a sample;

a uniquely-mapped reads determining unit, for determining uniquely-mapped reads aligned to a genome reference sequence based on obtained reads;

a number of uniquely-mapped reads calculating unit, for dividing the genome reference sequence into a plurality of windows, and calculating the number of uniquely-mapped reads falling into each of the plurality of windows a number of uniquely-mapped reads correcting unit, for subjecting the number of uniquely-mapped reads falling into each of the plurality of windows to a GC correction, and to a correction based on the expected number of uniquely-mapped reads adjusted by a control set to obtain the corrected number of uniquely-mapped reads;

a candidate breakpoint selecting unit, for calculating a significance value of the difference between two numerical populations each consisting of the corrected numbers of uniquely-mapped reads falling into windows on each of the two sides of a demarcation point, the demarcation point being a starting point or an ending point of each of the plurality of windows, to thereby select the demarcation point having a smaller significance value as a candidate CNV breakpoint;

a breakpoint determining unit, for calculating a significance value of the difference between two numerical populations each consisting of the corrected number of uniquely-mapped reads falling into windows contained within each of two sequences, with one sequence ranging from a given CNV breakpoint to an adjacent upstream CNV breakpoint, and the other sequence ranging from the given CNV breakpoint to an adjacent downstream CNV breakpoint, and for removing the candidate CNV breakpoint having the least significance at every turn and recalculating the significance value for the two candidate CNV breakpoints adjacent to the removed candidate CNV breakpoint, performing cyclic iteration until the significance values of all candidate CNV breakpoints are less than a termination threshold value, to thereby determine the CNV breakpoint.

Optionally, each of the plurality of windows can contain the same number of reference unique reads, or each of the plurality of windows may have the same length.

Optionally, the termination threshold value can be obtained based on the control set consisting of normal samples.

Optionally, the number of uniquely-mapped reads correcting unit comprises:

a GC correction module, for grouping the plurality of windows based on a GC content, and obtaining a correction coefficient based on a mean value of the number of uniquely-mapped reads within one group and a mean value of the number of uniquely-mapped reads for all of the plurality of windows, and then subjecting the number of uniquely-mapped reads falling into each of the plurality of windows to the correction, to obtain the GC-corrected number of uniquely-mapped reads;

a window correction module, for calculating a ratio of the GC-corrected number of uniquely-mapped reads falling into each of the plurality of windows in the control set to the total number of uniquely-mapped reads; obtaining a mean value of the ratios for all windows corresponding to the control set; and calculating the expect number of uniquely-mapped reads for each of the plurality of windows in the sample based on the obtained mean value of the ratios and the total number of uniquely-mapped reads in the sample.

Optionally, after the CNV breakpoint is determined by the breakpoint determining unit, the system can further comprise:

a breakpoint filtering unit, for determining a confidence interval of the normal corrected number of uniquely-mapped reads using the control set, based on a distribution of the corrected number of uniquely-mapped reads; and determining an abnormality presenting in a sequence between the two CNV breakpoints, if the mean value of the corrected number of uniquely-mapped reads within the sequence is outside the confidence interval.

Optionally, the corrected number of uniquely-mapped reads can fit a normal distribution, and the confidence interval can be 95%.

Optionally, in the candidate breakpoint selecting unit, a cyclization with a single chromosome or a whole genome is performed when selecting the candidate CNV breakpoint.

Optionally, the system can further comprise:

means for obtaining the sample from a human, with the sample comprising amniotic fluid obtained by amniocentesis, villus obtained by chorionic villi sampling, umbilical cord blood obtained by percutaneous umbilical blood sampling, spontaneous miscarrying fetus tissue or human peripheral blood;

and/or means for obtaining a genomic DNA of the sample by a DNA extraction method such as a salting-out method, a column chromatography method, a beads method, or a SDS method;

and/or means for subjecting the genome DNA of the sample to random fragmenting by enzyme digestion, pulverization, ultrasound, or HydroShear method, to obtain DNA fragments;
and/or
means for subjecting the DNA fragments to single-end sequencing or pair-end sequencing, to obtain the reads of the DNA fragments.

Optionally, different samples are distinguished by adding different indexes to each of the DNA fragments of the samples.

One of the advantages of the method of detecting a copy number variation and a system thereof according to embodiments of the present invention lies in having clinical feasibility, which can accurately detect the copy number variation including micro-deletion and micro-duplication.

BRIEF DESCRIPTION OF THE DRAWINGS

These and other aspects and advantages of embodiments of the present invention will become apparent and more readily appreciated from the following descriptions made with reference the accompanying drawings, in which.

DETAILED DESCRIPTION

Figure 1:
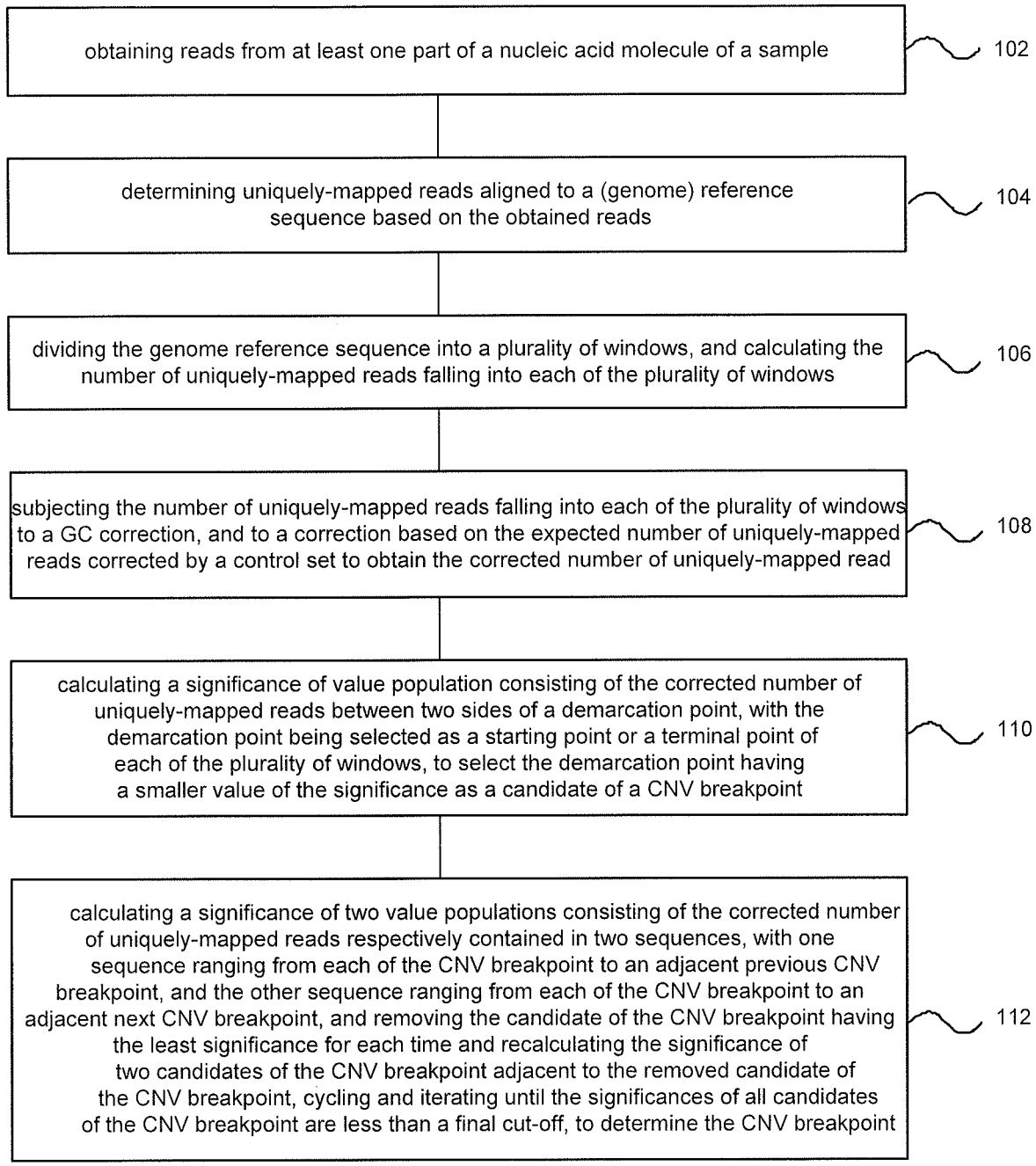
FIG. 1 is a flow chart showing a method of detecting a copy number variation according to an embodiment of the present invention.

Terms used herein are explained as below:

Copy number variation (CNV): refers to a change of copy number of at least a portion of a nucleic acid molecule in a sample to be tested as compared with the corresponding nucleic acid sequence in a normal sample, wherein the portion has a length of more than 1 kb. Cases and reasons for the copy number variation can include: deletion, such as micro-deletion; insertion, such as micro-insertion, micro-duplication, duplication; inversion, transposition and complex, multi-site variation.

Aneuploidy: refers to an addition or a reduction of the chromosome number presenting in a genetic material as compared with a normal sample, and can include an addition or reduction of an entire or partial chromosome. The copy number variation as used in the present disclosure can also include aneuploidy.

Sequencing: refers to a process of obtaining information of a nucleic acid sequence of a sample. The sequencing can be performed by various methods, including but not limited to, dideoxy chain termination; preferably a high-throughput sequencing method, including but not limited to, a Next-Generation sequencing technique or a single molecule sequencing technique.

The Next-Generation sequencing platform (Metzker ML. Sequencing technologies—the next generation. Nat Rev Genet. 2010 January; 11(1):31-46) includes, but are not limited to, Illumina-Solexa (GA™, HiSeq2000™, etc), ABI-Solid and Roche-454 (pryosequencing) sequencing platform; the single molecule sequencing platform (technique) includes, but are not limited to, True Single Molecule DNA sequencing of Helicos Company, single molecule real-time (SMRT™) of Pacific Biosciences Company, and nanopore sequencing technique of Oxford Nanopore Technologies Company (Rusk, Nicole (2009-04-01). Cheap Third-Generation Sequencing. Nature Methods 6 (4): 2446 (4)), etc.

A type of sequencing can be single-end sequencing and pair-end sequencing, a sequencing length can be 50 bp, 90 bp or 100 bp. In an embodiment of the present invention, the sequencing platform is Illumina/Solexa, the type of sequencing is pair-end sequencing, to obtain DNA sequence molecule having a length of 100 bp with a relationship of a bi-directional position.

In an embodiment of the present invention, a sequencing depth can be determined based on a length of variation fragment in a chromosome of a sample to be test. The higher sequencing depth, the higher sensitivity of the detection, i.e., the smaller length of deletion fragment and duplication fragment which can be detected. The sequencing depth can be 0.1-30×, i.e., the total amount is 0.1-30 folds in relative to a length of human genome, for example, in an embodiment of the present invention, the sequencing depth is $0.1 \times (2.5 \times 10^8 \text{ bp})$.

Reads: refers to a nucleic acid sequence having a certain length (generally longer than 20 bp), for example a sequencing result of the sequence generated by sequencer, which can be aligned to a specific region or location of a reference sequence by a sequence alignment method.

Sequence alignment (aligning): refers to a process of comparing one or more nucleic acid sequences to a reference sequence. Specifically, a nucleic acid sequence having a relative shorter length (such as a read) is aligned to a reference genome sequence, to determine a location of the nucleic acid sequence having the relative shorter length in the reference genome. When using a computer to perform sequence alignment, the sequence alignment can be performed by any one of sequence alignment procedures, such as ELAND (efficient local alignment of nucleotide data), SOAP (Short Oligonucleotide Analysis Package) and BWA (Burrows-Wheeler Aligner), etc. A standard for recognizing a successful alignment is classified into a non-fault-tolerant alignment (100% of matches) and partial-fault-tolerant alignment (less than 100% of matches).

Uniquely-mapped reads: refers to reads which can be aligned to a unique position of a reference sequence (for example a reference genome sequence).

Reference unique reads: refers to sequences having a fixed length and a uniquely-mapped position aligned to a reference sequence (generally a reference genome). A process of obtaining the reference unique reads, for example includes, dividing a reference genome into a plurality of sequences having a fixed length, aligning the plurality of sequences to the reference genome, selecting a sequence uniquely-aligned to the reference genome as a reference uniquely-mapped sequence. The fixed length is determined based on a sequence length of a sequencing result obtained by a sequencer, which can specifically refer to a mean length. Different sequencer can obtain sequencing results of different sequence length. Specific to every sequencing, the sequence length of the sequencing result can also be different, in which a certain subjective and experience factors can exist in the selection thereof.

Index: refers to a nucleic acid sequence having a specific length and playing a function as a marker. When DNA molecules to be tested derive from a plurality of samples to be tested, each of the plurality of samples can be added with different indexes, for distinguishing the plurality of samples during sequencing (Micah Hamady, Jeffrey J Walker, J Kirk Harris et al. Error-correcting barcoded primers for pyrosequencing hundreds of samples in multiplex. Nature Methods, 2008, March, Vol. 5 No. 3), to achieve subjecting the plurality of samples to simultaneous sequencing. The index is for distinguishing different sequences, without affecting other functions of the DNA molecule added with the index.

GC correction: a certain GC bias exists among batches or within one batch, which may cause copy number bias presenting in a region having a high GC content or a low GC content of a genome. The CG correction is performed with sequencing data based on a control set, to obtain corrected relative number of reads in each window, by which such bias can be eliminated, and an accuracy of detecting the copy number variation may be improved.

Mean value: generally refers to an arithmetic mean value or a median.

The number of uniquely-mapped reads: the number of uniquely-mapped reads can be statistic number obtained by calculating based on the initial number, or can be corrected value obtained by subjecting the number of uniquely-mapped reads to a correction with a correction coefficient, for example can be a ratio, in some cases can be interchangeable with "copy rate".

Sample to be tested: can also be called as a test sample in some cases, which refers to a sample including a nucleic acid molecule which is suspected having variation. A type of the nucleic acid is not subjected to special restriction, which can be deoxyribonucleic acid (DNA), or can be ribonucleic acid (RNA), preferably is DNA. RNA can be converted to DNA having a corresponding sequence by conventional means, for subsequent detections and analysis.

Control sample: is relative to the sample to be tested, which is regarded as a normal sample. Generally, normal means having a normal phenotype.

Control sample set (Control set): refers to a set consisting of the control samples, in an embodiment of the present invention, the number of the control samples in the control set is required to be more than 30.

Reference will be made in detail to embodiments of the present invention. The embodiments described herein with reference to drawings are explanatory, illustrative, and used to generally understand the present invention.

With continuous development of high-throughput sequencing technology and gradually decrease of sequencing cost, the sequencing technology has been increasingly and extensively applied in detection of chromosome variation.

Sequencing technology to detect chromosomal aberrations in terms of gaining are more widely used.

To improve the technology of detecting a copy number variation in clinic, the present invention designs a technical solution for screening the copy number variation in a whole genome level based on high-throughput sequencing technology, which has advantages of being high throughput, high specific and high accuracy of alignment. A detection result can be obtained by obtaining a sample from a subject; extracting DNA; high throughput sequencing, and subjecting obtained data to analysis.

FIG. 1 is a flow chart showing a method of detecting a copy number variation according to an embodiment of the present invention.

As shown in FIG. 1, in step 102, reads are obtained from at least one part of a nucleic acid molecule of a sample. At least one part of nucleic acid molecule or an entire nucleic acid molecule in a test sample can be subjected to sequencing to obtain reads. Reads of the part of nucleic acid molecule of the test sample can be obtained, or reads of the entire nucleic acid molecule can be obtained. For example, a genomic DNA molecule from a test sample is randomly fragmented to obtain DNA fragments, which are then subjected to sequencing to obtain reads having a certain length. The length of obtained reads can be within a certain range, and the reads having a fixed length can be obtained by truncating. The DNA fragments can have a length of 50 bp~1500 bp, such as, 50 bp~150 bp, 150 bp~350 bp, 350 bp~500 bp, 500 bp~700 bp, 700 bp~1000 bp or 1000 bp~1500 bp. For example, the DNA fragments can have a length of 50 bp, 90 bp, 100 bp, 150 bp, 300 bp, 350 bp, 500 bp, 700 bp, 1000 bp, 1500 bp. In an example, 300 bp~700 bp is preferred, 350 bp~500 bp is more preferred. The length of the reads can having a large difference due to different sequencer, for example, general sequence length of equipments such as illumina-solexa and life technologies-solid is within a range of 300 bp, while sequence length obtained by Roche-454, conventional Sanger sequencing, ultramodern single molecule sequencing system may be approximately or exceed 1000 bp. To meet an requirement for unique alignment, when selecting uniquely-mapped reads, sequences having a length of 20 bp or more are generally selected, preferably, selected sequences have a length of 26 bp or more.

Step 104, uniquely-mapped reads aligned to a genome reference sequence are determined based on the obtained reads. For example, entire or partial sequences of the reads are aligned to the genome reference sequence, to obtain site information of the reads in the genome, and further obtain site information of the reads on a specific chromosome. For a sample deriving from a human subject, the human genome reference sequence can be a human genome reference sequence in NCBI database. In an example of the present invention, the human genome reference sequence is a human genome reference sequence of Build 36 in NCBI database (hg18; NCBI Build 36), alignment software used is SOAPaligner/soap2. Those DNA fragment reads uniquely-mapped to the genome reference sequence are selected, namely, those reads uniquely-mapped to the genome reference sequence only one time, i.e., uniquely-mapped reads aligned to the (genome) reference sequence.

Step 106, the genome reference sequence is divided into a plurality of windows, and the number of uniquely-mapped reads falling into each of the plurality of windows is calculated. A method for detecting the plurality of windows may comprise: fragmenting a reference genome into fragments having a sequencing length being same as that of the sample to be tested, which are subjected to alignment by same alignment software with same parameter, to screen out uniquely-mapped positions on a chromosome; determining one of the plurality of windows by every interval having a certain length of the uniquely-mapped positions. A cross-sliding between the pluralities of the windows can or cannot exist depending on selection. The number of uniquely-mapped sites which can be included in the plurality of windows relates to sequencing data volume of the sample to be tested. Generally, the expected reads number of the sample to be tested falling into each of the plurality of windows is 300 or more, so as to guarantee the reads number falling into the plurality of windows fitting Poisson distribution. For example, assuming that the number of uniquely-mapped sites of a genome is N, effective reads number of the sample to be tested is n, and the expected number of reads falling into each of the plurality of windows in E, then each of the plurality of windows of the reference genome can include $$\frac{N}{n} \times E$$

of the uniquely-mapped sites.

Step 108, the number of uniquely-mapped reads falling into each of the plurality of windows is subjected to a GC correction, and to a correction based on the expected number of uniquely-mapped reads adjusted by a control set to obtain the corrected number of uniquely-mapped reads. In an example, the step of subjecting the number of uniquely-mapped reads falling into each of the plurality of windows to the GC correction and to a correction based on the expected number of uniquely-mapped reads adjusted by a control set to obtain the corrected number of uniquely-mapped reads further comprises:

grouping the plurality of windows based on a GC content, and obtaining a correction coefficient based on a mean value of the number of uniquely-mapped reads within one group and a mean value of the number of uniquely-mapped reads for all of the plurality of windows, and then subjecting the number of uniquely-mapped reads falling into each of the plurality of windows to the correction, to obtain the GC-corrected number of uniquely-mapped reads;

the expected number of uniquely-mapped reads adjusted by the control set is obtained by following steps:

calculating a ratio of the GC-corrected number of uniquely-mapped reads falling into each of the plurality of windows in the control set to the total number of uniquely-mapped reads;

obtaining a mean value of the ratios for all windows corresponding to the control set; and calculating the expect number of uniquely-mapped reads for each of the plurality of windows in the sample based on obtained mean value of the ratios and the total number of uniquely-mapped reads in the sample.

Step 110, a significance value of the difference between two numerical populations each consisting of the corrected numbers of uniquely-mapped reads falling into windows on each of the two sides of a demarcation point is calculated, with the demarcation point being a starting point or an ending point of each of the plurality of windows, to thereby select the demarcation point having a smaller significance value (i.e., more significant difference) as a candidate CNV breakpoint. For example, a predetermined number of windows are selected as candidate CNV breakpoints within a whole genome range based on a p value presenting a significance level of copy number variation between two sides of each of the plurality of windows, to obtain a significance value for each of the candidate CNV breakpoints, namely, a p value.

Step 112, a significance value of the difference between two numerical populations each consisting of the corrected number of uniquely-mapped reads falling into windows contained within each of two sequences is calculated, with one sequence ranging from a given CNV breakpoint to an adjacent upstream CNV breakpoint, and the other sequence ranging from the given CNV breakpoint to an adjacent downstream CNV breakpoint, and the candidate CNV breakpoint having the least significance is removed, and the significance value for the two candidate CNV breakpoints adjacent to the removed candidate CNV breakpoint is recalculated. This process is repeated until the significance values for all remaining candidate CNV breakpoints are less than a termination threshold value, to thereby determine the CNV breakpoint. The termination threshold value generally is preset. For example, the termination threshold value can be obtained by analyzing and processing a control set consisting of normal samples.

In the above examples, the selection of a CNV breakpoint is performed by: aligning the obtained reads to the genome reference sequence, calculating the number of uniquely-mapped reads falling into each of the plurality of windows, subjecting the number of uniquely-mapped reads falling into each of the plurality of windows to a GC correction and to a correction based on a control set, calculating and recalculating a significance value of difference to repeatedly select candidate CNV breakpoints, so as to achieve CNV detection. The method can accurately determine relatively small copy number variation including micro-deletion/micro-duplication.

For a sample derived from a human, the subject sample can be a genomic DNA obtained from amniotic fluid by amniocentesis, villus obtained by chorionic villi sampling, umbilical cord blood obtained by percutaneous umbilical blood sampling, spontaneous miscarrying fetus tissue or human peripheral blood. The genomic DNA can be extracted by conventional extraction methods such as a salting-out method, a column chromatography method, a beads method, or a SDS method. In an example, the column chromatography method is preferred, such column chromatography method can comprise: obtaining exposed DNA molecules by subjecting blood, tissue and cells to cell lysis buffer and proteinase K, and combining the DNA molecules to a silicone membrane under a condition of high salinity, and then eluting the DNA molecules from the silicone membrane under a condition of low salinity and high pH value. A specific principal and method can refer to specification of Tiangen TIANamp Micro DNA Kit (DP36).

If the DNA fragments to be detected are derived from a plurality of subject samples, the DNA fragments of each subject sample can be added with different indexes having a length of 4 bp to 12 bp, for distinguishing different sample during sequencing (Micah Hamady, Jeffrey J Walker, J Kirk Harris et al. Error-correcting barcoded primers for pyrosequencing hundreds of samples in multiplex. Nature Methods, 2008, March, Vol. 5 No. 3). By such, a plurality of subject samples can be subjected to simultaneous detection, which can improve efficiency and decrease detecting cost.

Figure 2:
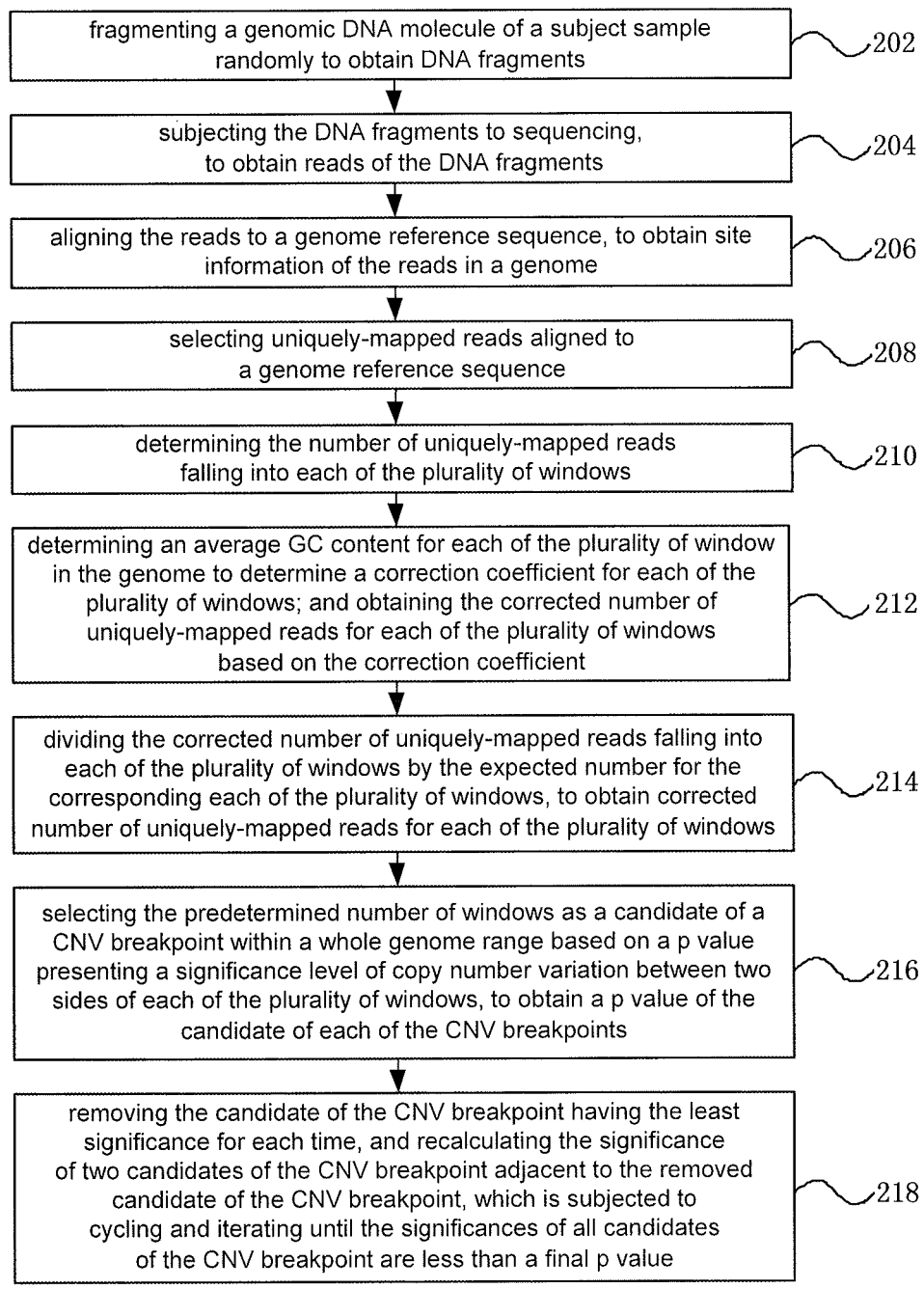
FIG. 2 is a flow chart showing a method of detecting a copy number variation according to another embodiment of the present invention.

FIG. 2 is a flow chart showing a method of detecting a copy number variation according to another embodiment of the present invention.

Step 202, a genomic DNA molecule of a subject sample is randomly fragmented to obtain DNA fragments, which can be performed by enzyme digestion, pulverization, ultrasound, or HydroShear method. The ultrasound method is preferably used, such as S-series from Covaris Company (based on AFA technique, when sound energy/mechanical energy released from a sensor passing through a DNA sample, gas is dissolved and forms a bubble. After the energy is removed, the bubble is ruptured to generate a capability for fragmenting the DAN fragments. By setting conditions such as a certain energy intensity and time interval, the DNA molecule can be fragmented into fragments having a certain size. A specific principal and method can refer to specification for S-series of Covaris Company), is used for fragmenting the DNA molecule into fragments having a certain concentrated size.

Step 204, the DNA fragments are subjected to sequencing, to obtain sequencing sequences of the DNA fragments, namely, reads. The reads obtained from sequencing can have a certain length within a range. The reads having a fixed length can be obtained by subjecting reads of the DNA fragments to truncation. The reads of the DNA fragments used in the present example hereafter refer to reads having a fixed length. Methods used for sequencing may be high-throughput sequencing methods such as Illumina/Hiseq2000, ABI/SOLiD, Roche/454. Sequencing type may be Single-end sequencing or Pair-end sequencing, and sequencing length may be 50 bp to 1500 bp. In an example of the present invention, the used sequencing platform is Illumina/Hiseq2000, the sequencing type is Pair-end sequencing, and obtained DNA sequence molecules with a length of 100 bp has a relationship of a bi-directional position. The sequencing depth can be determined based on the length of variation fragment in a chromosome. The higher sequencing depth, the higher sensitivity of the detection, i.e., the smaller length of deletion fragment and duplication fragment which can be detected. In an example of the present invention, the sequencing volume of the human subject sample ranges of $2\sim900\times10^8$ of reads.

Step 206, the reads are aligned to a genome reference sequence, to obtain site information of the reads in a genome.

Step 208, uniquely-mapped reads aligned to a genome reference sequence is selected.

Step 210, the number of uniquely-mapped reads falling into each of the plurality of windows is determined. For each subject sample, the number of uniquely-mapped reads falling into each of the plurality of windows is calculated (recorded as $n_{i,j}$, subscripts I and j respectively represent No. of the plurality of window and No. of the subject samples, for distinguishing which are omitted for brevity).

Step 212, an average GC content for each of the plurality of window in the genome is determined to determine a correction coefficient for each of the plurality of windows; and the corrected number of uniquely-mapped reads for each of the plurality of windows is obtained based on the correction coefficient. Such step is mainly to subject the number of uniquely-mapped reads falling into each of the plurality of windows to the correction based on the GC content for each of the plurality of windows, which can be called as batches correction or GC correction.

The average GC content (recorded as $GC_{i,j}$) of the uniquely-mapped reads falling into each of the plurality of windows is calculated. The calculation of the average GC content ($GC_{i,j}$) includes calculating average GC content of all uniquely-mapped reads falling into each of the plurality of windows. During calculation, the total number of bases G and C of all uniquely-mapped reads is recorded as $N_{gc}$, a total length of all uniquely-mapped reads is recorded as L, then $$GC_{i,j} = \frac{N_{gc}}{L}.$$

To correct a difference of data volume of the subject sample, each of the plurality of windows are grouped based on $GC_{i,j}$, i.e., windows having same $GC_{i,j}$ are grouped into one group, a median or an arithmetic mean value $m_{g,j}$ for the number of uniquely-mapped reads in each group is determined, which is divided by a median or an arithmetic mean value $m_j$ for the number of uniquely-mapped reads in the whole genome level, to obtain the correction coefficient $c_{g,j}$ ($c_{g,j}=m_{g,j}/m_j$), in which the subscript g represents GC contents of different groups. The original number of uniquely-mapped reads falling into each of the plurality of windows $n_{i,j}$ is multiplied by the correction coefficient $c_{g,j}$ to obtain a corrected value of the number of uniquely-mapped reads falling into each of the plurality of windows (recorded as $n_{i,j}'$).

Step 214, the corrected number of uniquely-mapped reads falling into each of the plurality of windows is divided by the expected number for the corresponding each of the plurality of windows, to obtain corrected number of uniquely-mapped reads for each of the plurality of windows, i.e., copy rate. The expected number for the corresponding each of the plurality of windows is obtained by a control set consisting of normal samples. Such steps is mainly to subject the number of uniquely-mapped reads for each of the plurality of windows to correction based on data of normal samples, which can be called as window correction.

In the sample of control set, a percentage of relative number of uniquely-mapped reads ($P_{i,j}$) is defined as a ratio of the number of uniquely-mapped reads within a window ($n_{i,j}'$) to the total number of uniquely-mapped reads for the whole genome ($N_j$), i.e., $$P_{i,j} = \frac{n_{i,j}'}{N_j};$$

and then an average percentage of each of the plurality of windows in the control set $\overline{P_i}$ is calculated, i.e., $$\overline{P_i} = \frac{1}{n}\sum_{j=1}^{n} P_{i,j}.$$

In the subject sample, the copy rate of each of the plurality of windows $r_{i,j}$ is obtained by dividing the corrected number of uniquely-mapped reads $n_{i,j}'$ by the expected number within the window (multiplying the total number of uniquely-mapped reads for the whole genome with the percentage of the number of uniquely-mapped reads falling into each of the plurality of windows), i.e., $$r_{i,j} = \frac{n_{i,j}'}{\overline{P_i} \times N_j}.$$

In selecting the control set, the method of library construction, sequencing reagent and sequencing type should be consistent with the sample to be tested as much as possible, so as to improve effect of correcting the sample to be tested by the control sample. The sample in the control set should be a normal sample with a sample volume of 30 or more.

Step 216, a predetermined number of windows are selected as candidate CNV breakpoints within a whole genome range based on a p value presenting a significance value of copy number variation between the two sides of each of the plurality of windows, and the p value for each of the candidate CNV breakpoints is obtained.

1) Selection of the candidate CNV breakpoints: for all windows of the whole genome, calculating a difference of copy number variations between the two sides of each of the plurality of windows, each consisting of a certain number of windows (the number of windows is normally more than 30 or satisfies a restriction of the lowest sample amount for a detection model, in order to make the detection model to detect significant difference); and selecting a certain number (for example, 1% of the total number of windows) of sites (corresponding to the plurality of windows) as the candidate CNV breakpoints (namely, a demarcation point of each CNV fragments), based on the significant difference level in the whole genome range (from small value to large value of the p value). 2) Initialization: a set of all ranked breakpoints is recorded as $B_c=\{b_1, b_2, \ldots b_k \ldots, b_s\}$, then two adjacent breakpoints k+1 and k−1 exist at two sides of the breakpoint k. By calculating a significance value for the difference between a set of copy numbers falling into the windows in a sequence from k−1 to k and a set of copy numbers falling into windows in a sequence from k to k+1, a p value representing a significance difference between the two sides of breakpoint k is obtained. For example, in an example, a Run test in non-parameter detection is selected, which evaluates the significant difference of two populations by homogeneous status of distribution with mixed elements of the two populations, specifically referring to Wald, A. & Wolfowitz, J. On a test whether two samples are from the same population. The Annals of Mathematical Statistics 11, 147-162 (1940).

Step 218, the candidate CNV breakpoint having the least significance is removed, and the significance values for the two candidate CNV breakpoints adjacent to the removed candidate CNV breakpoint are recalculated. This process is repeated until the significance values for all candidate CNV breakpoints are less than a final p value (i.e., a termination threshold value), which is obtained based on the control set.

Iteration merger: the candidate breakpoints having the least significance is removed from each round of cycling and iterating, and the p values for the two adjacent breakpoints are recalculated until all of the p values are less than the final p value.

The final p value is obtained by: for example, subjecting the control samples to the above operation of Iteration merger; recording the largest p value for each Iteration merger; performing the above operation of Iteration merger until merging into one fragment. By then, according to a change trend of the largest p value, the largest p value for one time of Iteration merger corresponding to one site having the most dramatic change of the p value (i.e., selecting one site having the most obvious change of slope in a curve of the p value change (a site having the largest curvature)) or that of the previous time of Iteration merger is taken as the termination threshold value.

The above steps 216 and 218 can also be called as fragmentation. Notice: when selecting the windows and the breakpoints in 1) and 2) of the step 214, a cyclization with a single chromosome or a whole genome can be considered to be performed. The cyclization with the single chromosome refers to: when calculating the plurality of windows near the starting point of a chromosome, if the effective window number on the left side is insufficient for statistical detection, then sufficient number of windows for calculation is obtained reversely from the end point of such chromosome; in a similar way, for those positions, of which the sufficient effective number of windows near the right side of the end point is not able to be obtained, are obtained from the front point of the chromosome. Such operation makes those windows located at the front point and the end point still can be calculated. The cyclization with the whole genome is: indexing the end point of the former chromosome when the effective number of windows located at the front point of each chromosome, while indexing the front point of the latter chromosome when the effective number of windows located at the end point is insufficient, while chromosome 1 connects to chromosome Y.

After the step 218, the method further comprises subjecting the sequence between two CNV breakpoints to a confidence selection, in which the confidence selection comprises steps of: determining a confidence interval of normal copy rate using the control set, based on a distribution of the copy rate; and determining an abnormality presenting in the sequence between the two CNV breakpoints, if the mean value of the copy rate within the sequence is outside the confidence interval. In an example, the copy rate the copy rate fits a normal distribution, and the confidence interval is 95%. The fragmenting result is subjected to a filtration by such step, to obtain a reliable result. If the mean value of $r_{i,j}'$ is smaller than a lower cut-off value or larger than an upper cut-off value, then a corresponding result is output as a positive result.

Selection of termination threshold value can comprise: calculating a distribution of copy rate for a window in each of the control samples, which is based on central-limit theorem, in which reads in the window are random, then the copy rate r fits a normal distribution, and quantiles of the left and the right with a significance level being as 0.05 are selected. A mean value thereof is calculated in the control set, which are taken as the upper and lower threshold value for screening copy number variation.

In the above examples, accuracy of detection result is improved by the batches correction and the window correction. By introducing the control set, accuracy can also be improved by enlarging the control set, which can reduce requirement for initial DNA amount.

Figure 3:
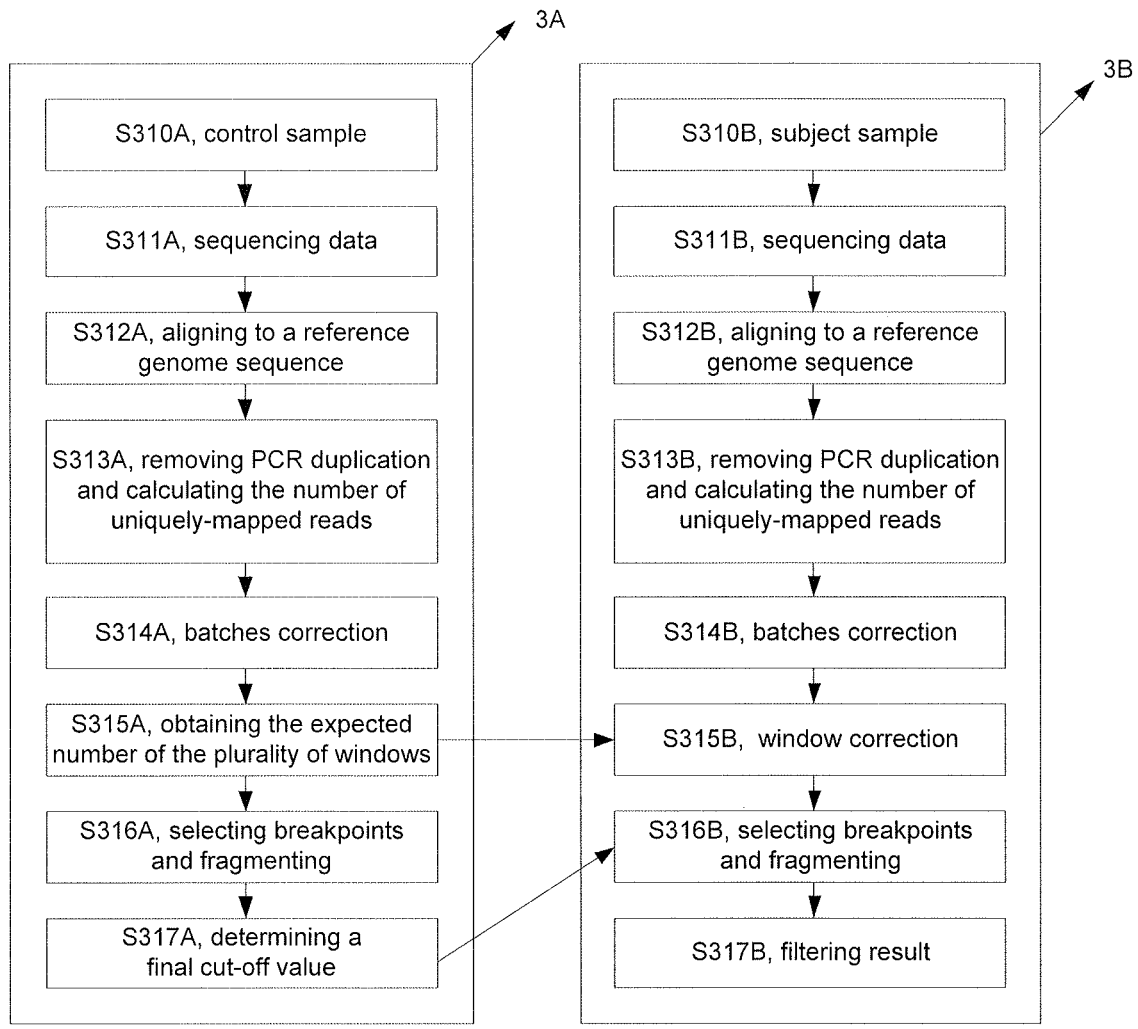
FIG. 3 is a flow chart showing a method of detecting a copy number variation according to a further embodiment of the present invention.

FIG. 3 is a flow chart showing a method of detecting a copy number variation according to a further embodiment of the present invention. FIG. 3 includes a flow chart showing a method of handling a control set consisting of normal samples (3A) and a flow chart showing a method of handling a subject sample (3B). The control set is mainly used for obtaining data for correcting the subject sample, and for the termination threshold value being as a terminating condition of iterating the subject sample.

As shown in FIG. 3, the flow chart 3A comprises:

Step 301A, extracting DNA molecule from the control sample;

Step 311A, randomly fragmenting the DNA molecule of the control sample into DNA fragments, which are then subjected to sequencing, to obtain sequencing sequence data of the DNA molecule of the control sample, i.e., reads;

Step 312A, aligning the reads of the control sample to a reference genome sequence;

Step 313A, calculating the number of uniquely-mapped reads falling into each of the plurality of windows, i.e., the number of uniquely-mapped reads;

Step 314A, subjecting the control sample to the batches correction;

Step 315A, obtaining the expected number of the plurality of windows by the control sample, for subjecting the control sample to the window correction.

Step 316A, selecting breakpoints and fragmenting. The step of selecting a candidate CNV breakpoint comprises: removing the candidate CNV breakpoint having the least significance and recalculating the p value of the two candidate CNV breakpoints adjacent to the removed candidate CNV breakpoint, cycling and iterating until the number of rest fragments equals to a predetermined value (such as 24).

Step 317A, determining a termination threshold value. By calculating a mean value of current final p value, the final p value can be effectively obtained, as the termination threshold value of the condition for terminating iteration with the subject sample.

Step 3B comprises:

Step 310B, extracting DNA molecule of a subject sample;

Step 311B, randomly fragmenting the DNA molecule of the control sample into DNA fragments, which are then subjected to sequencing, to obtain reads of the DNA molecule of the control sample;

Step 312B, aligning the reads of the DNA molecule of the control sample to a reference genome sequence;

Step 313B, calculating the number of uniquely-mapped reads falling into each of the plurality of windows, i.e., the number of uniquely-mapped reads.

Step 314B, subjecting the subject sample to batches correction.

Step 315B, subjecting the subject sample to window correction based on the expected number of uniquely-mapped reads falling into each of the plurality of windows for the control sample;

Step 316B, selecting breakpoints and fragmenting;

Step 317B, subjecting obtained result to filtering.

For selecting the control set, a method of library constructing, sequencing reagent and sequencing type should be consistent with the sample to be tested as much as possible, so as to improve effect of correcting the sample to be tested by the control sample. The sample in the control set should be a normal sample with a sample volume being 30 or more.

Figure 4:
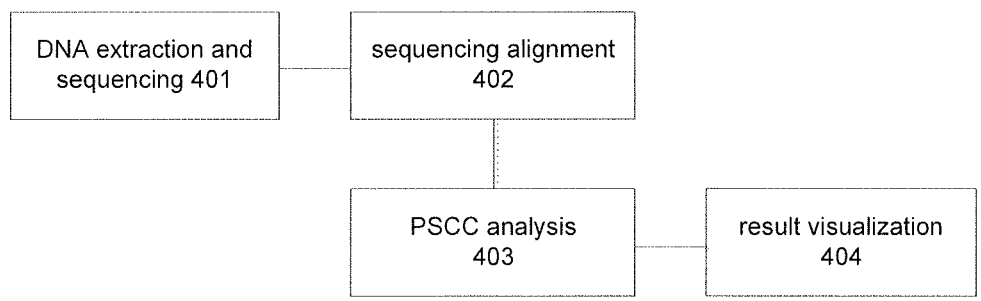
FIG. 4 is a brief flow chart showing a method of chromosomal CNV analysis according to an embodiment of the present invention.

FIG. 4 is a brief flow chart showing a method of chromosomal CNV analysis according to an embodiment of the present invention.

As shown in FIG. 4, step 401 is DNA extraction and sequencing: after genomic DNA is extracted in accordance with specification of Tiangen DP327-02 Kit, a library is constructed in accordance to a process of library construction based on Illumina/Hiseq2000 standard. During such process, those DNA molecules concentrating in 500 bp are ligated with adaptors at both ends thereof for sequencing, in which each sample is also added with different indexes respectively, by which data from the plurality of samples can be distinguished in a result of sequencing for one time.

Step 402, sequence alignment: A sequencing method of Illumina/Hiseq2000 is used for sequencing (other sequencing methods such as ABI/SOLiD can also achieve a same or similar effect), each sample can obtain reads of DNA fragments having a certain length, which is aligned to a standard human genome reference sequence in NCBI database using SOAP2, to obtain information of a corresponding position where the reads locate in the genome. To avoid interference of repetitive sequence to CNV analysis, only those reads uniquely mapped to the human genome reference sequence are selected, i.e., those reads can be mapped to the human genome reference sequence only once, also called as the number of uniquely-mapped reads, as the effective data for subsequent CNV analysis.

Step 403, PSCC analysis. A serious of bioinformatics methods of detecting a copy number variation in a whole genome copy which are independently developed by the inventor of the present invention are utilized, which comprises: subjecting the subject sample to batches correction, subjecting the subject sample to window correction based on a control set, normalization and fragmentation (segmentation).

Step 404, the fragments having the determined copy number in the step 403 are subjected to CNV analysis, a copy rate≤0.7 and a copy rate≥1.3 of the subject sample are taken as a cut-off value for detecting deletion and duplication of the fragments, by which the fragments having the copy number variation in a whole genome level is obtained by analysis, and then obtained result is subjected to visualization.

In the above examples, used software algorithm is a series procedure of detecting a copy number variation for a whole genome developed by Shenzhen BGI, which are called as PSCC. It can generate data by the Next-Generation sequencing technology, subjecting the subject sample to batches correction, and performing data correction with a control set, normalization and segmentation, to estimate degree and size of copy number variation of the subject sample. Under a condition of a lower sequencing depth (50 M of sequencing short-sequences), about 0.5 Mb of fragments having a single copy number variation (CNV) can be detected.

Figure 5:
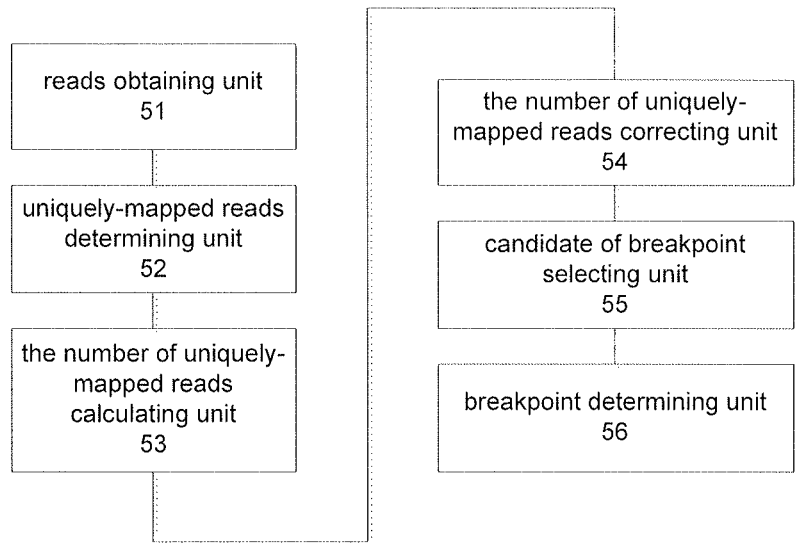
FIG. 5 is a schematic diagram showing a system of detecting a copy number variation according to an embodiment of the present invention.

FIG. 5 is a schematic diagram showing a system of detecting a copy number variation according to an embodiment of the present invention. As shown in FIG. 5, the system can comprise: a reads obtaining unit 51, for obtaining reads from at least one part of a nucleic acid molecule of a sample; a uniquely-mapped reads determining unit 52, for determining uniquely-mapped reads aligned to a genome reference sequence based on obtained reads; the number of uniquely-mapped reads calculating unit 53, for dividing the genome reference sequence into a plurality of windows, and calculating the number of uniquely-mapped reads falling into each of the plurality of windows; the number of uniquely-mapped reads correcting unit 54, for subjecting the number of uniquely-mapped reads falling into each of the plurality of windows to a GC correction, and to a correction based on the expected number of uniquely-mapped reads adjusted by a control set to obtain the corrected number of uniquely-mapped reads; a candidate breakpoint selecting unit 55, for calculating a significance value of the difference between two numerical populations each consisting of the corrected numbers of uniquely-mapped reads falling into windows on each of the two sides of a demarcation point, with the demarcation point being a starting point or an ending point of each of the plurality of windows, to thereby select the demarcation point having a smaller value of the significance as a candidate CNV breakpoint; a breakpoint determining unit 56, for calculating a significance value of the difference between two numerical populations each consisting of the corrected number of uniquely-mapped reads falling into windows contained within each of two sequences, with one sequence ranging from a given CNV breakpoint to an adjacent upstream CNV breakpoint, and the other sequence ranging from the given CNV breakpoint to an adjacent downstream CNV breakpoint, and removing the candidate CNV breakpoint having the least significance and recalculating the significance values for the two candidate CNV breakpoints adjacent to the removed candidate CNV breakpoint, cycling and iterating until the significances of all candidate CNV breakpoint are less than a termination threshold value, to thereby determine the CNV breakpoint; the termination threshold value is obtained based on the control set consisting of normal samples. When the number of uniquely-mapped reads calculating unit 53 divides the plurality of windows, each of the plurality of windows can contain the same number of reference unique reads, or each of the plurality of windows can have a same length. In an example, in the candidate breakpoint selecting unit 55, a cyclization with a single chromosome or a whole genome is performed when selecting the candidate CNV breakpoint.

In the above examples, the uniquely-mapped reads determining unit determines uniquely-mapped reads which can be uniquely aligned to the (genomic) reference sequence based on obtained reads, the number of uniquely-mapped reads correcting unit subjects the number of uniquely-mapped reads falling into each of the plurality of windows to a correction, and the candidate breakpoint selecting unit and the breakpoint determining unit perform cycling and iterating of gene significant difference for selecting the CNV breakpoints, by which CNV detection can be completed, which can accurately detect a region comprising the copy number variation including smaller micro-deletion/micro-duplication.

Figure 6:
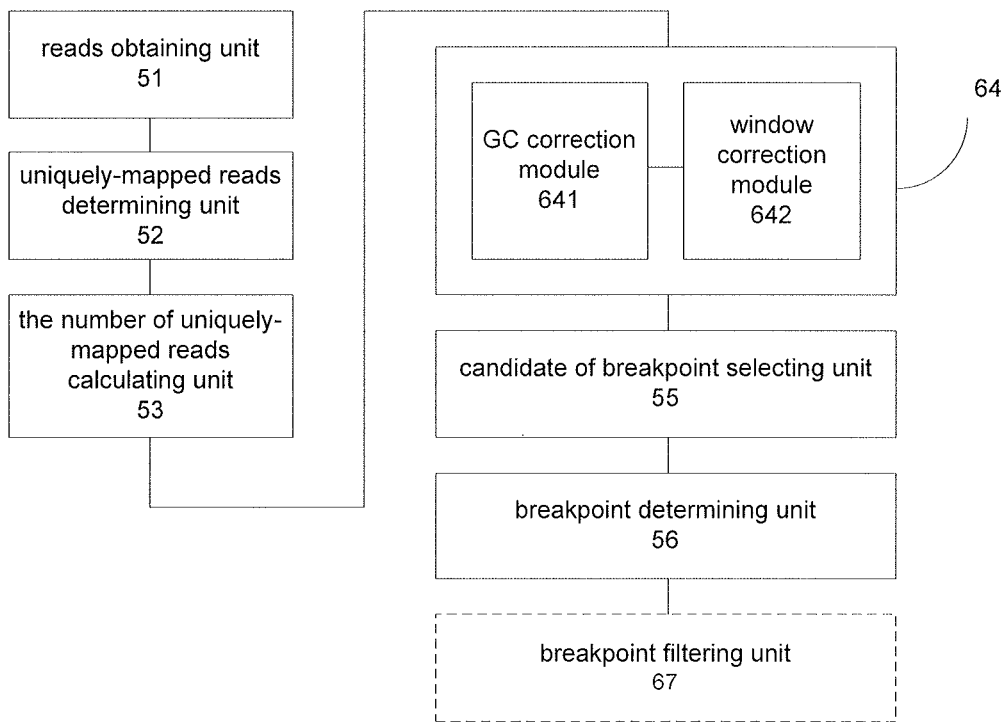
FIG. 6 is a schematic diagram showing a system of detecting a copy number variation according to anther embodiment of the present invention.
Figure 7A:
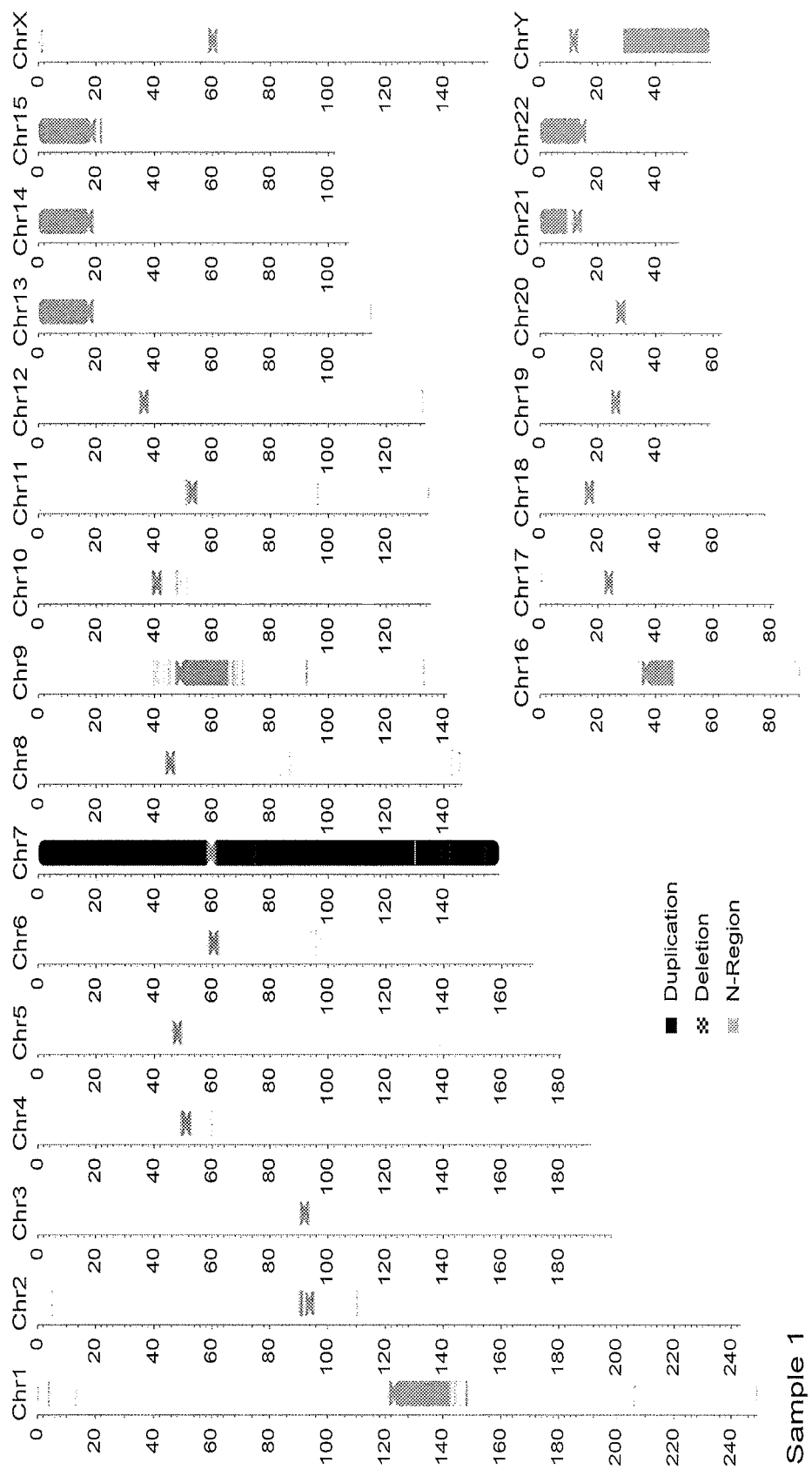
FIG. 7A-7H show detection results of eight samples respectively analyzed in an example of the present invention.
Figure 7B:
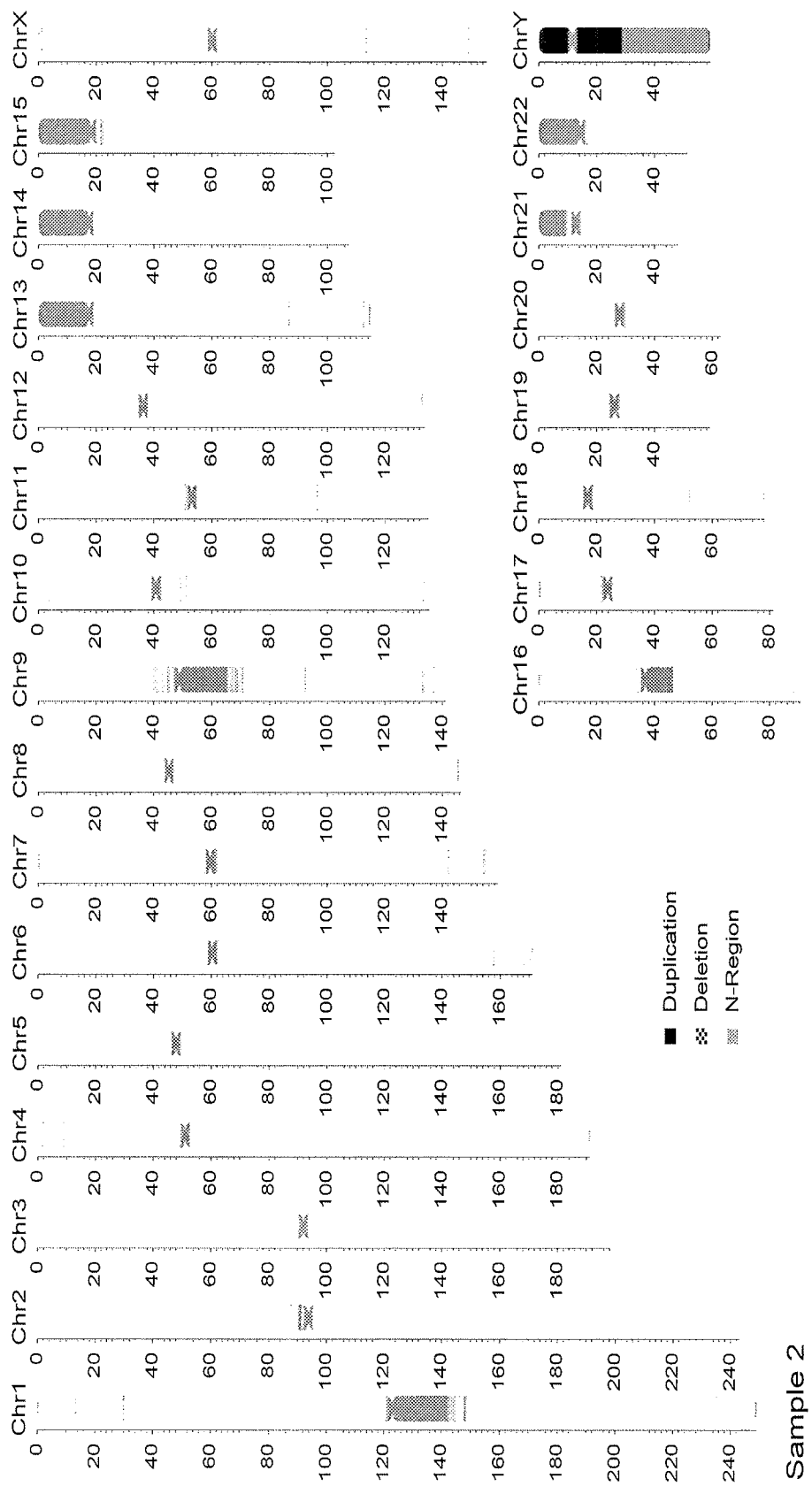
Figure 7C:
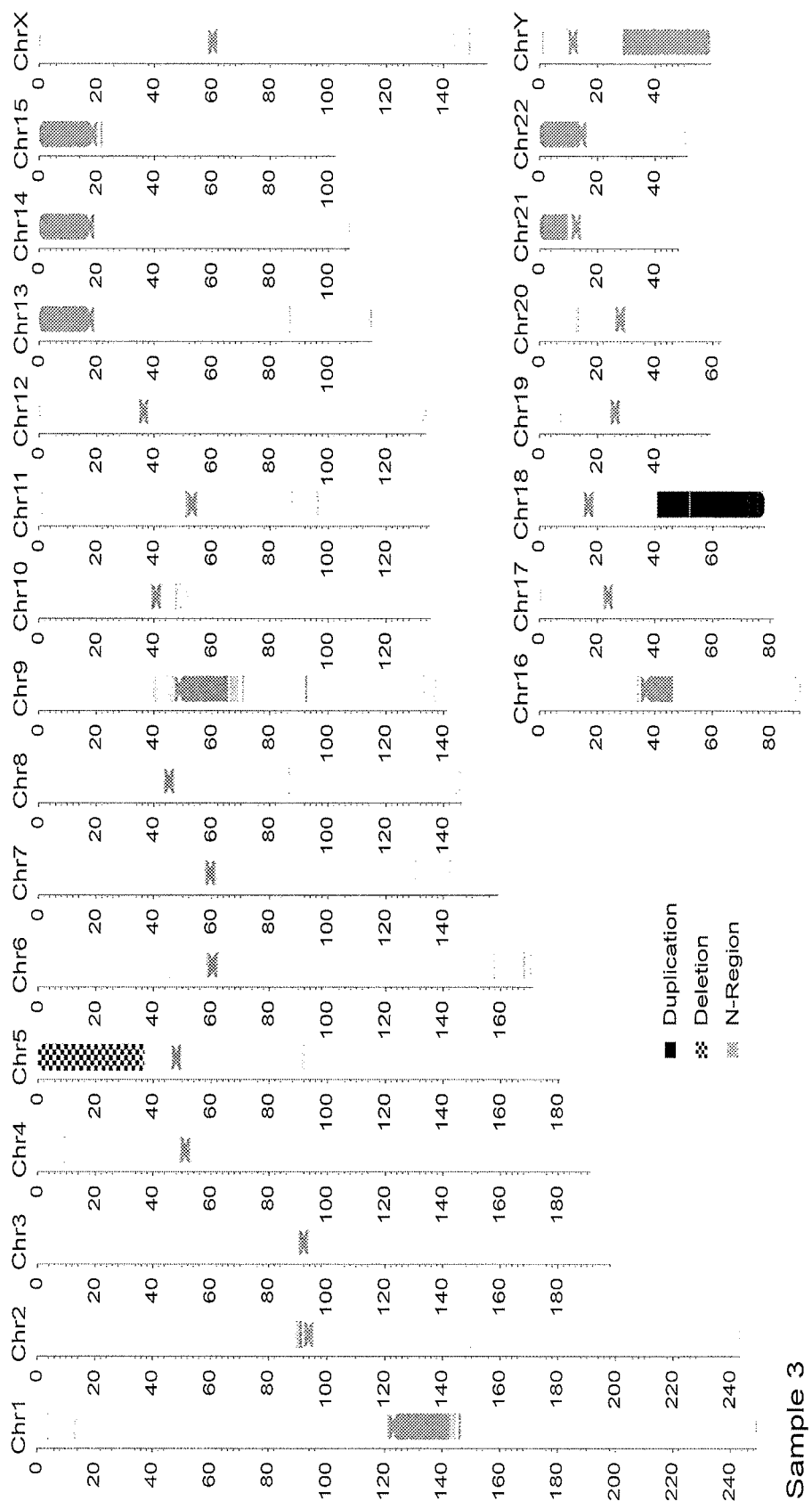
Figure 7D:
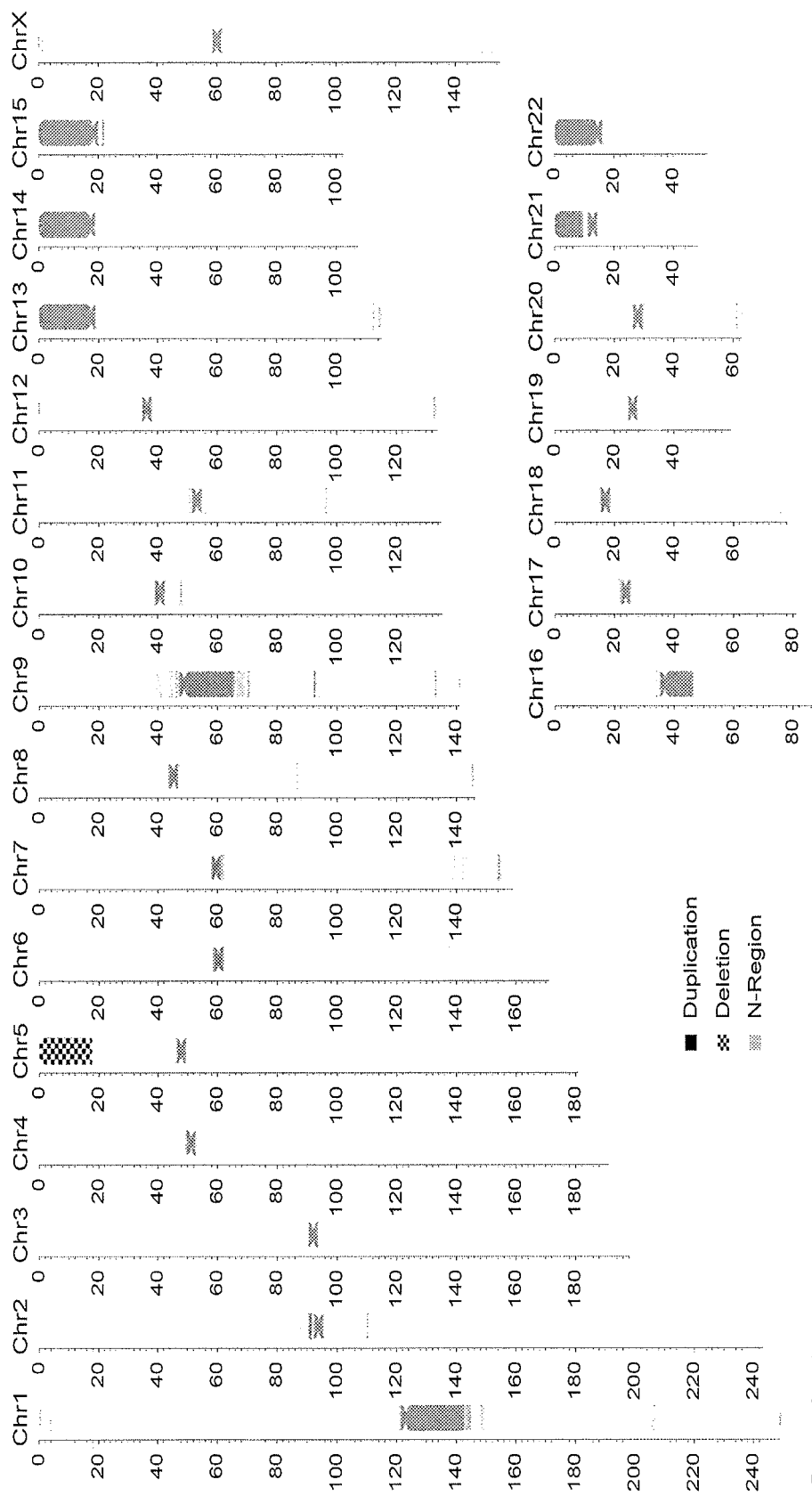
Figure 7E:
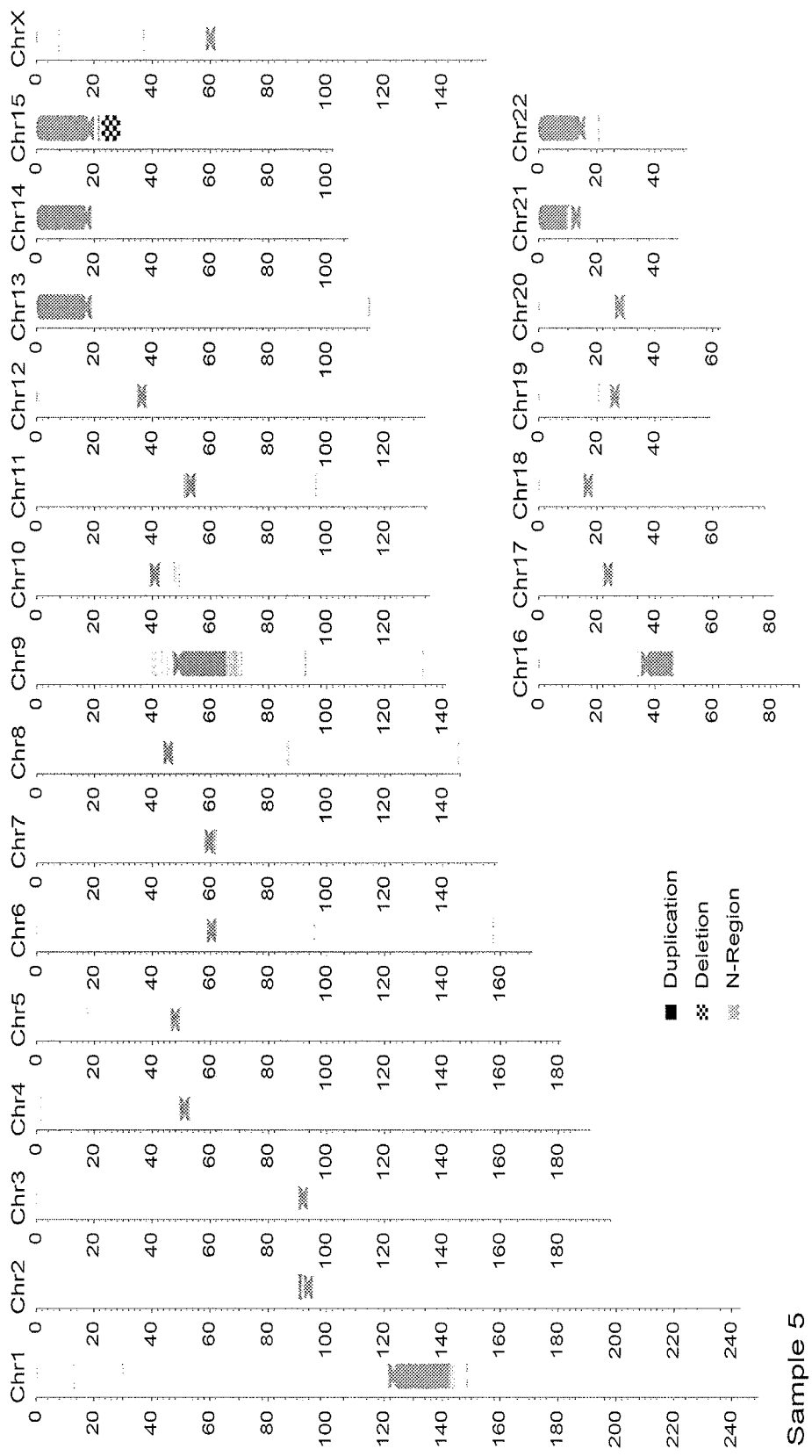
Figure 7F:
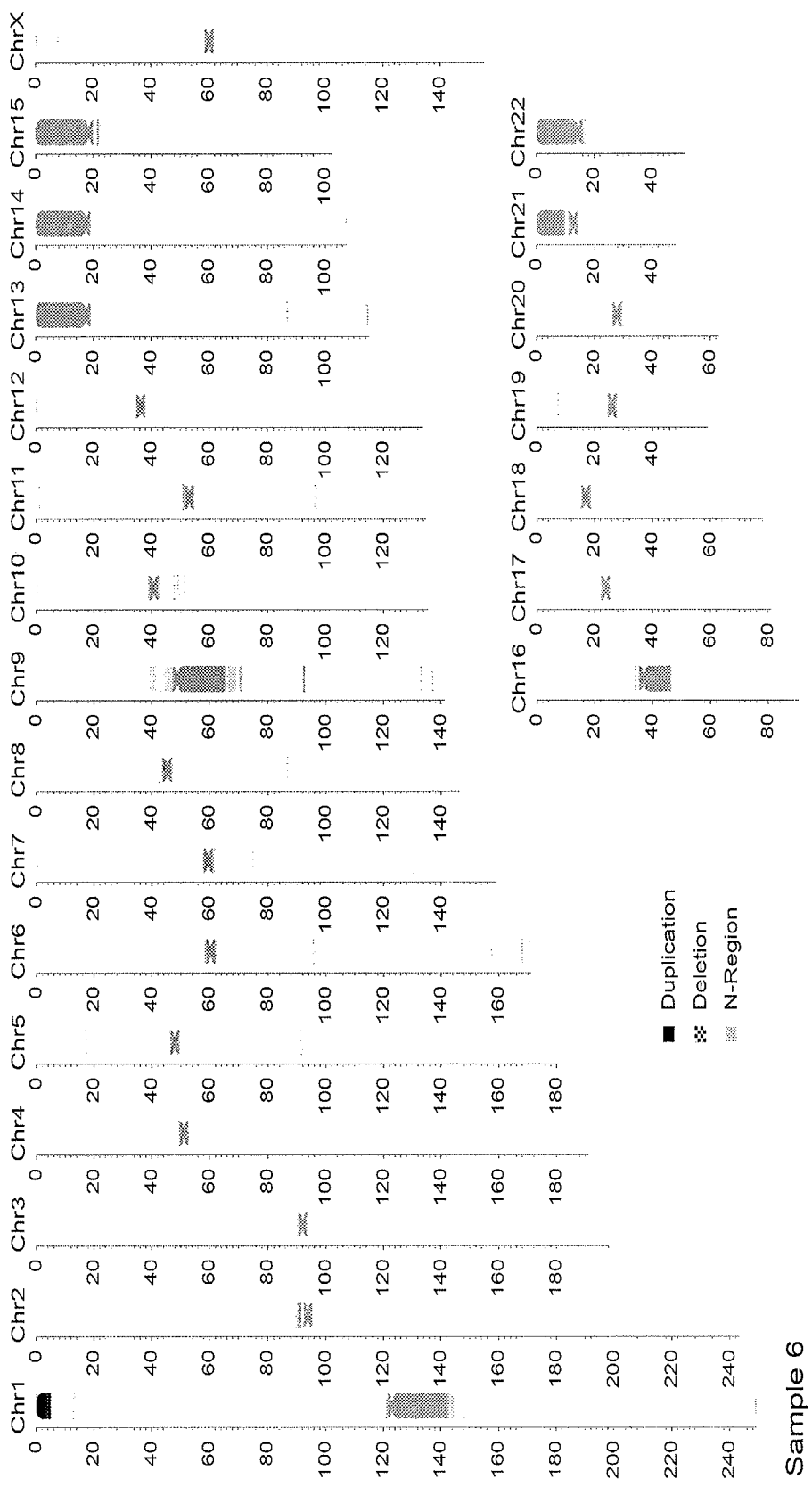
Figure 7G:
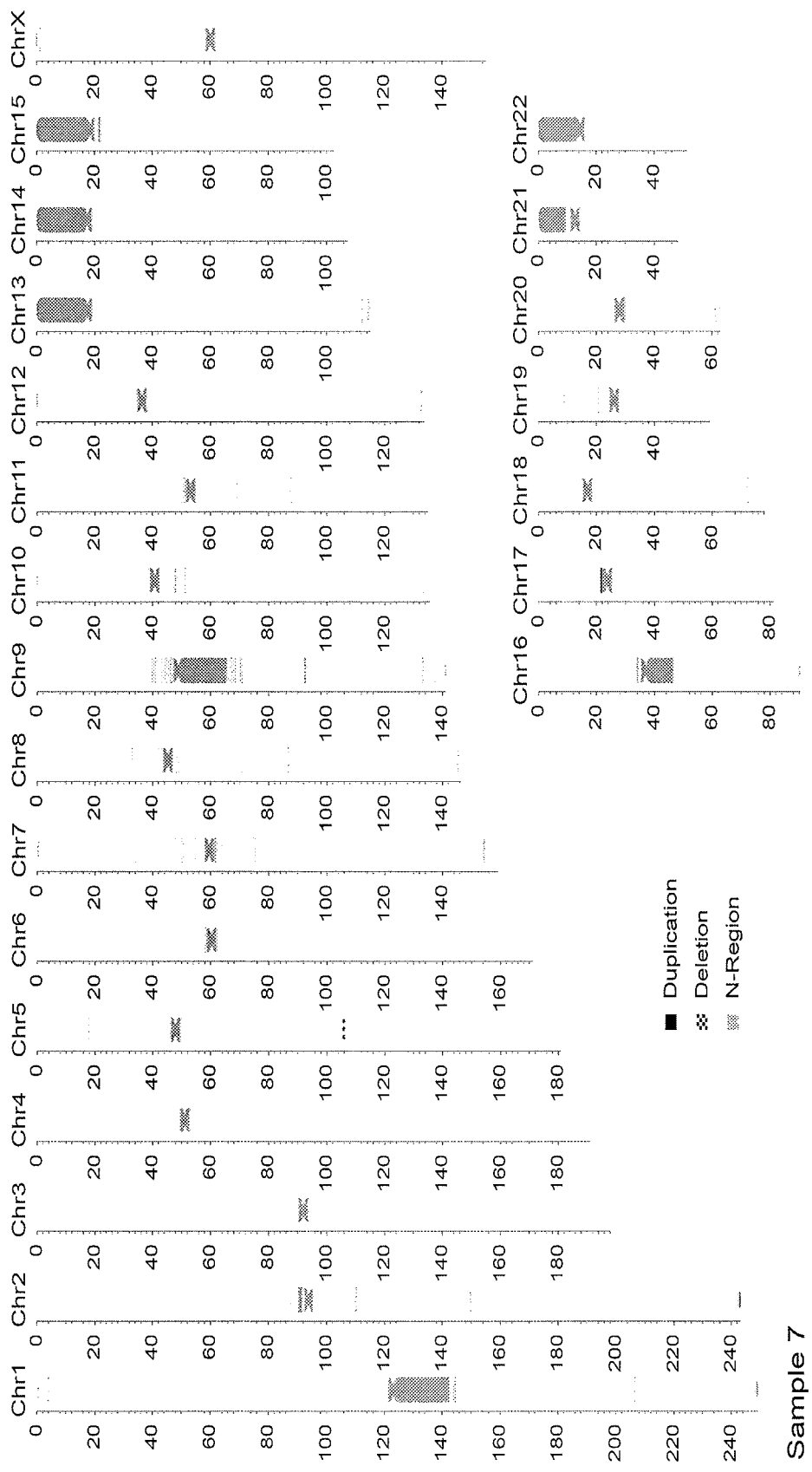
Figure 7H:
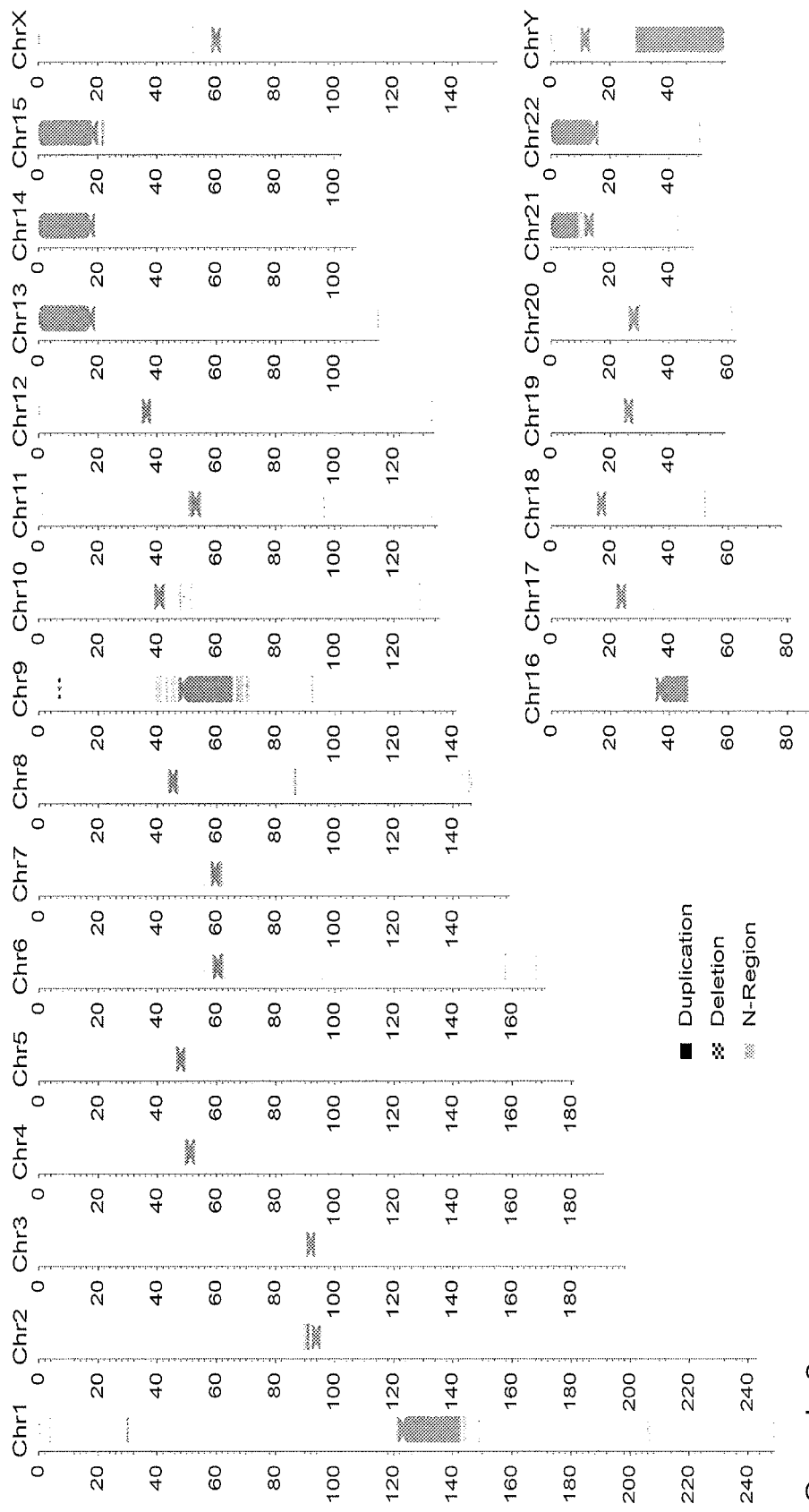

FIG. 6 is a schematic diagram showing a system of detecting a copy number variation according to anther embodiment of the present invention. As shown in FIG. 6, the system comprises: a reads obtaining unit 51, a uniquely-mapped reads determining unit 52, the number of uniquely-mapped reads calculating unit 53, the number of uniquely-mapped reads correcting unit 64, a candidate breakpoint selecting unit 55 and a breakpoint determining unit 56. The reads obtaining unit 51, the uniquely-mapped reads determining unit 52, the number of uniquely-mapped reads calculating unit 53, the candidate breakpoint selecting unit 55 and the breakpoint determining unit 56 can refer to specific description in FIG. 5, which is omitted for brevity. The number of uniquely-mapped reads correcting unit 64 further includes a GC correction module 641 and a window correction module 642. In which, the GC correction module is used for grouping the plurality of windows based on a GC content, and obtaining a correction coefficient based on a mean value of the number of uniquely-mapped reads within one group and a mean value of the number of uniquely-mapped reads for all of the plurality of windows, and then subjecting the number of uniquely-mapped reads falling into each of the plurality of windows to the correction, to obtain the GC-corrected number of uniquely-mapped reads; the window correction module 642 is used for calculating a ratio of the GC-corrected number of uniquely-mapped reads falling into each of the plurality of windows in the control set to the total number of uniquely-mapped reads; obtaining a mean value of the ratios for all windows corresponding to the control set; and calculating the expect number of uniquely-mapped reads for each of the plurality of windows in the sample based on obtained mean value of the ratios and the total number of uniquely-mapped reads in the sample, also called as copy rate.

In an example of the present invention, the system further comprises: a breakpoint filtering unit 67, for determining a confidence interval of the normal corrected number of uniquely-mapped reads using the control set, based on a distribution of the corrected number of uniquely-mapped reads; and determining an abnormality presenting in the sequence between the two CNV breakpoints, if the mean value of the corrected number of uniquely-mapped reads within the sequence is outside the confidence interval. In an example, the corrected number of uniquely-mapped reads fits a normal distribution, and the confidence interval is 95%.

In an example, the system further comprises: means for obtaining the sample from a human, with the sample comprising amniotic fluid obtained by amniocentesis, villus obtained by chorionic villi sampling, umbilical cord blood obtained by percutaneous umbilical blood sampling, spontaneous miscarrying fetus tissue or human peripheral blood; and/or means for obtaining a genomic DNA of the sample by a DNA extraction method such as a salting-out method, a column chromatography method, a beads method, or a SDS method; and/or means for subjecting the genome DNA of the sample to random fragmenting by enzyme digestion, pulverization, ultrasound, or HydroShear method, to obtain DNA fragments; and/or means for subjecting the DNA fragments to single-end sequencing or pair-end sequencing, to obtain the reads of the DNA fragments. In an example, different samples are distinguished by adding different indexes to each of the DNA fragments of the samples.

Functions of each unit in FIG. 5 and FIG. 6, can refer to specification of the corresponding part above according to the method in examples of the present invention, which are omitted for brevity.

Those skilled in the art will recognize hardware, firmware and software configurations in these cases are interchangeable, to achieve the function of each specific application as much as possible.

Reference will be made in detail to examples of the present invention. It would be appreciated by those skilled in the art that the following examples are explanatory, and cannot be construed to limit the scope of the present invention. If the specific technology or conditions are not specified in the examples, a step will be performed in accordance with the techniques or conditions described in the literature in the art or in accordance with the product instructions. If the manufacturers of reagents or instruments are not specified, the reagents or instruments can be commercially available. Descriptions in following brackets respectively illustrate catalog No. of different manufacturers for various reagents or kits. The adaptor and index used for sequencing derive from Multiplexing Sample Preparation Oligonutide Kit of Illumina Company.

Application Example 1

Detection with 2 Samples Having Chromosome Number Variation and 6 Samples Having Micro-Deletion 1. DNA Extraction 8 samples (hereinafter referred as Sample1, Sample2, Sample3, . . . , Sample8) were subjected to DNA extraction in accordance with specification of TIANamp Micro DNA Kit (DP316) of Tiangen. The extracted DNA was subjected to library construction in accordance with revised specification of Illumina/Hiseq2000. Those DNA molecules concentrating in a length of 500 bp were ligated with an adaptor at both ends thereof for sequencing. Each sample was added with different indexes respectively, which were then subjected to hybridization with a complementary adaptor on Flowcell surface, by which nucleic acid molecules clustering grew under a certain condition, which were then subjected to Pair-end sequencing on Illumina Hiseq2000, to obtain sequences of DNA fragments having a length of 100 bp.

In details, about 100 ng of DNA obtained from the above amniotic fluid sample (Quant-IT dsDNA HS Assay kit), were subjected to library construction in accordance with revised specification of Illumina/Hiseq2000, of which detailed procedure could refer to prior art (specification of standard library construction of Illumina/Solexa provided in website: www.illumina.com). The obtained DNA library and insert fragments were determined having a length of 500 bp using 2100Bioanalyzer (Agilent), which were subjected to sequencing on computer after accurate quantification by QPCR.

2. Sequencing: in the current example, above DNA obtained from the 8 samples were subjected to sequencing on computer in accordance with specifications of Cluster-Station and Hiseq2000 (PEsequencing) officially published by Illumina/Solexa, to obtain about 5G of data volume for each sample, which were distinguished by ligated indexes. Using alignment software SOAP2, DNA sequence obtained by sequencing was aligned to a human genome reference sequence Build 36 in NCBI database (hg18; NCBIBuild36), to obtain information of a corresponding position where the reads locate in the genome.

3. Data Analysis a) basic statistics: calculating the number of uniquely-mapped reads falling into each of the plurality of windows (i.e., the number of uniquely-mapped reads, recorded as $n_{i,j}$, subscripts I and j respectively represented No. of the plurality of window and No. of the subject samples, for distinguishing, which are omitted for brevity), and an average GC content (recorded as $GC_{i,j}$).

b) batches correction: to correct a difference of sample data volume, the plurality of windows were grouped based on the average GC content of reads falling into thereof. A median or an arithmetic average for each group was divided by a median or an arithmetic average for the whole genome, to obtain a correction coefficient $c_g$, in which the subscript g represented GC contents of different groups. The original number of uniquely-mapped reads falling into each of the plurality of windows $n_{i,j}$ was multiplied by the correction coefficient $c_g$ to obtain a corrected value of the number of uniquely-mapped reads falling into each of the plurality of windows (recorded as $n_{i,j}'$).

c) data correction: sequencing data obtained from 90 samples in YH population were selected as the control set. In the sample of control set, a percentage of relative number of uniquely-mapped reads ($P_{i,j}$) was defined as a ratio of the corrected number of uniquely-mapped reads within a window ($n_{i,j}'$) to the total number of uniquely-mapped reads for the whole genome ($N_j$), i.e., $$P_{i,j} = \frac{n_{i,j}'}{N_j};$$

and then an average percentage of each of the plurality of windows in the control set $\overline{P_i}$ was calculated, i.e., $$\overline{P_i} = \frac{1}{n}\sum_{j=1}^{n} P_{i,j}.$$

In the subject sample, the copy rate of each of the plurality of windows $r_{i,j}$ was obtained by dividing the corrected number of uniquely-mapped reads $n_{i,j}'$ by the expected number within the window (multiplying the total number of uniquely-mapped reads for the whole genome with the percentage of the number of uniquely-mapped reads falling into each of the plurality of windows), i.e., $$r_{i,j} = \frac{n_{i,j}'}{\overline{P_i} \times N_j}.$$

d) fragmentation (segmentation)

① selection of a candidate breakpoint: for all $r_{i,j}$ in the whole genome, calculating a difference in copy number changes between two sides of a point, each side having 100 windows; and selecting 10000 points with the most significant differences as the candidate CNV breakpoints, based on the significant difference level in the whole genome range (from small value to large value of the p value).

② initialization: a set of all ranked breakpoints was recorded as $B_c=\{b_1, b_2, \ldots b_k \ldots, b_s\}$, then two adjacent breakpoints k+1 and k−1 existed at two sides of breakpoint k. By calculating a significance value of the difference between a set of copy numbers falling into windows from k−1 to k and a set of copy numbers falling into windows from k to k+1, a p value representing a significant difference between the two sides of breakpoint k was obtained (a Run test of non-parameter detection was used in the current example).

③ Iteration merger included: by continuous cycling and iterating, the candidate breakpoints having the least significance is removed from each round, and the p values for the two adjacent breakpoints are recalculated until all of the p values are less than $1E^{-50}$.

Notice: when selecting the windows and the breakpoints in steps ① and ②, a cyclization with the whole genome was performed, to ensure that those windows located at the front point and the end point of a chromosome still can be calculated.

e) termination threshold value and filtration: a result obtained after fragmentation was subjected to filtering. If the mean value of $r_{i,j}'$ for a fragment was smaller than 0.7 or larger than 1.3, a corresponding result was output as a positive result.

f) visualization of the positive result

4. Statistical calculation

For the 8 samples, the detection result and verification result were shown in details in Table below.

In particular, the verification result was obtained by CGH chip (comparative genomic hybridization chip). Human Genome CGH Microarray Kit (Agilent Technologies Inc.) was used in the experiments in accordance with specification provided by manufacturer.

TABLE 1

CNV results of 8 samples

| Sample No. | Detection result | length | Verification result | Determination |
|---|---|---|---|---|
| Sample1 | T7 | 159.14 M | T7 | consistent |
| Sample2 | XYY | 59.37 M | XYY | consistent |
| Sample3 | chr5: 1 . . . 36877903 deletion chr18: 39024931 . . . 76038278 addition | 36.88 M 37.01 M | 5p15.3~p13.2 (183931~36816731) × 1; 18p12.3~q23 (39086755~76067279) × 3 | consistent |

TABLE 1-continued

CNV results of 8 samples

| Sample No. | Detection result | length | Verification result | Determination |
|---|---|---|---|---|
| Sample4 | chr5: 1 . . . 17710089 deletion | 17.71 M | 5p15.33~p15.1 × 1 | consistent |
| Sample5 | chr15: 21236149 . . . 26219186 deletion | 4.98 M | 15q11.2~q13.1 × 1 | consistent |
| Sample6 | chr1: 1 . . . 5065299 addition | 5.07 M | 1p36.33~p36.32 × 3 | consistent |
| Sample7 | chr5: 105562861 . . . 106156933 deletion | 0.59 M | 5q21.3 × 1 | consistent |
| Sample8 | chr9: 6851755 . . . 7248416 deletion | 0.40 M | 9p24.1 × 1 | consistent |

In Table 1, chr represented chromosome, T7 represented trisomy of chromosome 7, and XYY represented trisomy variation of sex chromosome.

FIG. 7A-7H show detection results of eight samples respectively in an example of the present invention.

It could be seen from the above Table 1 and FIG. 7A-7H that, as small as 0.4M of fragments having micro-deletion and as large as entire chromosome number variation could be accurately detected and located by the method of the present invention, which demonstrated the excellent efficiency and accuracy of the present invention.

Comparing with those analysis methods for detecting the copy number variation that have been reported thus far, advantages of the present invention mainly include:

1) resolution: by using about 50 M of data, a region of 0.5 M having micro-deletion can be accurately detected.

2) expandability: in addition to increasing sequencing volume, the accuracy is also improved by enlarging the control set, which can reduce requirement for initial DNA amount.

3) more stable and more comprehensive: there is few detailed description in reported articles, while the present disclosure describes various aspects such as batch correction and population correction with data, as well as optimization with condition for fragmentation, etc.

The method of the present invention can be used for whole genome copy number variation detection in the target patients, which can facilitate genetic counseling, provide basis for clinical decision, and make an accurate pathology determination for patients suffering from micro-deletion syndrome. The target patients of the present invention can be patients suffering from micro-deletion or potential carriers. The examples of target patients are used for illustrating the present invention, and should not be used to limit the scope of the present invention.

Although illustrative embodiments have been shown and described, it would be appreciated by those skilled in the art that the above embodiments cannot be construed to limit the present invention, and changes, alternatives, and modifications can be made in the embodiments without departing from the spirit, principles and scope of the present invention.

What is claimed is:

1. A computer-implemented method of detecting a copy number variation (CNV) comprising following steps:
    obtaining $2-900\times10^8$ reads from at least one part of a nucleic acid molecule of a sample using a method comprising subjecting the at least one part of the nucleic acid molecule of the sample to sequencing, to obtain the reads, wherein the sequencing is single-end sequencing or pair-end sequencing with a sequencing length of 50 bp to 1500 bp,
    determining uniquely-mapped reads aligned to a genomic reference sequence based on the obtained reads,
    dividing the genomic reference sequence into a plurality of windows, wherein dividing the genomic reference sequence into a plurality of windows comprises:
    fragmenting a reference genome into fragments having a sequencing length being the same as that of the at least one part of the nucleic acid molecule of the sample being tested,
    aligning the fragments of the reference genome to the at least one part of the nucleic acid molecule of the sample being tested to screen out uniquely-mapped positions on a chromosome, and
    determining one of the plurality of windows by every interval having a certain length of the uniquely-mapped positions such that the number of reads of the at least one part of the nucleic acid molecule of the sample being tested falling into each of the plurality of windows is 300 or more, so as to enable the number of reads falling into the plurality of windows to fit Poisson distribution,
    calculating the number of uniquely-mapped reads falling into each of the plurality of windows,
    subjecting the number of uniquely-mapped reads falling into each of the plurality of windows to a GC correction, and to a correction based on an expected number of uniquely-mapped reads adjusted by a control set to obtain a corrected number of uniquely-mapped reads,
    calculating a p value representing a significance difference between two numerical populations each consisting of the corrected numbers of uniquely-mapped reads falling into windows on each of the two sides, k+1 and k−1, of a demarcation point, k, the demarcation point being a starting point or an ending point of each of the plurality of windows, to thereby select the demarcation point having a smaller p value as a candidate CNV breakpoint;
    calculating a p value representing a significance difference between two numerical populations each consisting of the corrected number of uniquely-mapped reads falling into windows contained within each of two sequences, with one sequence ranging from a given candidate CNV breakpoint to an adjacent upstream candidate CNV breakpoint, and the other sequence ranging from the given candidate CNV breakpoint to an adjacent downstream candidate CNV breakpoint, and
    removing the candidate CNV breakpoint having the least significance from each calculation and recalculating the p value for the two candidate CNV breakpoints adjacent to the removed candidate CNV breakpoint, performing cyclic iteration until the p values of all candidate CNV breakpoints are less than a termination threshold value, to thereby determine the CNV breakpoint.

2. The method of claim 1, wherein each of the plurality of windows contains the same number of reference unique reads, or each of the plurality of windows has the same length.

3. The method of claim 1, wherein the step of subjecting the number of uniquely-mapped reads falling into each of the plurality of windows to the GC correction and to a correction based on the expected number of uniquely-mapped reads adjusted by the control set to obtain the corrected number of uniquely-mapped reads further comprises one or more selected from the group consisting of:
grouping the plurality of windows based on a GC content, and obtaining a correction coefficient based on a mean value of the number of uniquely-mapped reads within one group and a mean value of the number of uniquely-mapped reads for all of the plurality of windows, and then subjecting the number of uniquely-mapped reads falling into each of the plurality of windows to the correction, to thereby obtain the GC-corrected number of uniquely-mapped reads; and
obtaining the expected number of uniquely-mapped reads adjusted by the control set by following steps:
calculating a ratio of the GC-corrected number of uniquely-mapped reads falling into each of the plurality of windows in the control set to the total number of uniquely-mapped reads;
obtaining a mean value of the ratios for all windows corresponding to the control set; and
calculating the expect number of uniquely-mapped reads for each of the plurality of windows in the sample based on obtained mean value of the ratios and the total number of uniquely-mapped reads in the sample.

4. The method of claim 3, wherein a cyclization with a single chromosome or a whole genome is performed when selecting the candidate CNV breakpoint.

5. The method of claim 1, wherein after the CNV breakpoint is determined, the method further comprises:
subjecting a sequence between two CNV breakpoints to a confidence selection, wherein the confidence selection comprises steps of:
determining a confidence interval of the normal corrected number of uniquely-mapped reads using the control set, based on a distribution of the corrected number of uniquely-mapped reads; and
determining an abnormality presenting in the sequence between the two CNV breakpoints, if the mean value of the corrected number of uniquely-mapped reads within the sequence is outside the confidence interval.

6. The method of claim 5, wherein the corrected number of uniquely-mapped reads fits a normal distribution, and the confidence interval is 95%.

7. The method of claim 1, wherein the method further comprises one or more selected from the group consisting of:
obtaining the sample from a human, the sample comprising amniotic fluid obtained by amniocentesis, villus obtained by chorionic villi sampling, umbilical cord blood obtained by percutaneous umbilical blood sampling, spontaneous miscarrying fetus tissue or human peripheral blood;
obtaining a genomic DNA of the sample by a DNA extraction method such as a salting-out method, a column chromatography method, a beads method, or a SDS method;
subjecting the genome DNA of the sample to random fragmenting by enzyme digestion, pulverization, ultrasound, or HydroShear method, to obtain DNA fragments; and
subjecting the DNA fragments to single-end sequencing or pair-end sequencing, to obtain the reads of the DNA fragments.

8. The method of claim 1, wherein the method further comprises:
adding different indexes to each of the DNA fragments of the samples, to distinguish different samples.

9. The method of claim 1, wherein the sample is obtained from a subject in need of determining the copy number variation.

10. The method of claim 1, wherein dividing the genomic reference sequence into a plurality of windows further comprises:
performing a cross-sliding between the pluralities of the windows.

* * * * *